(12) United States Patent
Tolosa et al.

(10) Patent No.: US 7,718,353 B2
(45) Date of Patent: May 18, 2010

(54) PROTEINS, SENSORS, AND METHODS OF CHARACTERIZING ANALYTES USING THE SAME

(75) Inventors: Leah Tolosa, Columbia, MD (US); Govind Rao, Columbia, MD (US); Xudong Ge, Ellicott City, MD (US)

(73) Assignee: University of Maryland Baltimore County, Baltimore, MD (US)

( * ) Notice: Subject to any disclaimer, the term of this patent is extended or adjusted under 35 U.S.C. 154(b) by 1078 days.

(21) Appl. No.: 10/552,164

(22) PCT Filed: Mar. 1, 2004

(86) PCT No.: PCT/US2004/006276

§ 371 (c)(1),
(2), (4) Date: Oct. 11, 2005

(87) PCT Pub. No.: WO2004/101769

PCT Pub. Date: Nov. 25, 2004

(65) Prior Publication Data

US 2008/0261255 A1    Oct. 23, 2008

Related U.S. Application Data

(60) Provisional application No. 60/469,560, filed on May 9, 2003.

(51) Int. Cl.
*C12Q 1/00*    (2006.01)

(52) U.S. Cl. .......................................................... 435/4
(58) Field of Classification Search ...................... None
See application file for complete search history.

(56) References Cited

U.S. PATENT DOCUMENTS 6,197,534 B1 *  3/2001  Lakowicz et al. ............. 435/14
6,277,627 B1 *  8/2001  Hellinga ................... 435/287.1

OTHER PUBLICATIONS

Kella et al. "Fluorescence energy transfer studies on lima bean lectin", JBC, 1984, 259(8):4777-4781.*
Leah Tolosa, et al., "Reagentless optical sensing of glutamine using a dual-emitting glutamine-binding protein", Anal. Biochem., vol. 314, No. 2, pp. 199-205, (Mar. 15 2003).

* cited by examiner

*Primary Examiner*—Karen Cochrane Carlson
*Assistant Examiner*—Bin Shen
(74) *Attorney, Agent, or Firm*—René A. Vazquez

(57) ABSTRACT

A protein sensing molecule is capable of binding an analyte in a sample. The protein sensing molecule includes a first detectable quality that changes in a concentration dependent manner when the protein sensing molecule is bound to the analyte. The protein sensing molecule also includes a second detectable quality that does not undergo substantial change when the protein sensing molecule is bound to the analyte. The protein sensing molecule may be used in methods for characterizing samples and may also be used in sensors.

16 Claims, 22 Drawing Sheets

SEQUENCE LISTING

```
<160> NUMBER OF SEQ ID NOS: 2

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcactggcgg gcaccgtatg caacgatgct aacaacc                              37

<210> SEQ ID NO 2
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggttgttagc atcgttgcat acggtgcccg ccagtgc                              37
```

PROTEINS, SENSORS, AND METHODS OF CHARACTERIZING ANALYTES USING THE SAME

The present application claims priority of International Application No. PCT/US2004/006276, filed Mar. 1, 2004, published on Nov. 25, 2004, Publication No. WO 2004/101769 in the English language and claims priority to U.S. Provisional Application No. 60/469,560, filed May 9, 2003, which is incorporated by reference herein.

Part of the work performed during the development of this invention utilized U.S. government funds. The U.S. government may therefore have certain rights in this invention.

BACKGROUND OF THE INVENTION

1. Field of the Invention

The present invention relates to proteins, such as labeled proteins, sensors, and the characterization of analytes in a sample using the proteins.

2. Background of the Related Art

Analyte-binding proteins have many applications. The process of analyte binding often results in useful changes in the protein, such as a change in conformation of the protein.

For example, analyte-binding proteins may be used as sensor proteins to characterize samples. Sample characterization is a broad field that includes, e.g., determining the presence or concentration of analytes, biomedical diagnostics, bioprocessing, and drug screening.

Analyte measurement/detection has many applications. For instance, the increasing demand for the production of important biological products by eukaryotic cell cultures has intensified efforts in the development of sensing devices for monitoring nutrient levels, available oxygen, and cell density in bioreactors. For example, glutamine is a major source of nitrogen and carbon in cell culture media. Glutamine sensing is important in small and large-scale bioprocesses involving eukaryotic cell culture.

Glutamine is considered together with glucose as a limiting factor in cell growth and product yield. Additionally, unfavorable levels of glutamine can lead to the deleterious production of ammonia, which is toxic to cell cultures. Monitoring of glutamine concentrations is therefore an important aspect of process control.

Currently available glutamine biosensors tend to rely on enzymes such as glutaminase (EC 3.5.1.2) in combination with glutamate oxidase (EC 1.4.3.11). Glutamate oxidase is required to suppress the interference from glutamic acid. In another assay, glutamine reacts with three different enzymes to produce NADH, which is then determined spectrophotometrically. High-pressure liquid chromatography and LCMS-MS have been used, but these techniques both require expensive instrumentation. Near-infrared (NIR) spectroscopy allows for noninvasive quantification of glutamine but requires the generation of an elaborate calibration model.

Binding proteins have also been used to measure sugars and sugar derivatives, such as glucose. Glucose is the major carbon and energy source in cellular metabolism. The lack of glucose in a medium will severely limit cell growth and product yield in industrial bioprocess applications. But excessive glucose can also be detrimental, leading to lactate formation via the glycolytic pathway. Therefore, glucose monitoring and control is important for healthy growth of cells and maximum product formation in bioprocesses.

Another example of analyte measurement involves glucose measurement for diabetes treatment. To control the long-term complications associated with diabetes, blood glucose levels must be tightly regulated. This requires careful monitoring of blood glucose.

In view of the above, binding proteins have been utilized as sensors for various analytes including glucose, maltose, phosphate, and glutamine. One advantage of the binding proteins as sensors is that unlike enzymes, they do not require additional reagents. The key event that accompanies molecular recognition between a binding protein and its substrate is a conformational change.

Most binding proteins have a two-domain structure connected by a hinge, as disclosed in QUIOCHO, Phil. Trans. Roy. Soc. London, ser B, 326:341-351 (1990), which is incorporated by reference herein. The binding site is in the interface of the two domains. It has been shown in a number of proteins that binding of the ligand can induce a large conformational change, from an "open" ligand-free structure to a "closed" ligand-bound structure, as disclosed in HSIAO et al., J. Mol. Biol., 262:225-242 (1996); and SUN et al., J. Mol. Biol., 278:219-229 (1998), both of which are incorporated by reference herein. By introducing single fluorophores into such proteins, this conformational change upon ligand binding can be taken advantage of to construct biosensors that respond to their respective ligands. These binding proteins include glucose-binding protein (GBP) MARVIN et al., J. Am. Chem. Soc., 120:7-11 (1998); SALINS et al., Anal. Biochem., 294:19-26 (2001); and TOLOSA et al., Anal. Biochem., 267:114-120 (1999), which are all incorporated by reference herein), maltose-binding protein (GILARDI et al., Anal. Chem., 66:3840-3847 (1994); and GILARDI et al., Prot. Eng., 10(5):479-486 (1997), both of which are incorporated by reference herein), phosphate-binding protein (BRUNE et al., Biochemistry, 33:8262-8271 (1994), which is incorporated by reference herein), and glutamine-binding protein (GlnBP) (DATTELBAUM et al., Anal. Biochem., 291:89-95 (2001), which is incorporated by reference herein).

The choice of labeling sites is generally based on the identification of specific sites on the protein that undergo maximum conformational change upon substrate binding, as disclosed in MARVIN et al., J. Am. Chem. Soc., 120:7-11 (1998), which is incorporated by reference herein. However, this approach neglects the effects on the dye conjugated to the protein. Thus, it is common to observe different environment-sensitive dyes conjugated to the same site showing varying response to analyte concentrations, as disclosed in DATTELBAUM et al., Anal. Biochem., 291:89-95 (2001); and MARVIN et al., J. Am. Chem. Soc., 120:7-11 (1998), both of which are incorporated by reference herein. Consequently, there is a degree of empiricism in the design of binding protein-based biosensors.

One approach to biosensors involves genetically engineering a protein for site-specific positioning of allosteric signal transducing molecules. Structural principles are used to take advantage of cooperative interactions between the signaling molecule and analyte binding. This technique has been applied to maltose binding protein and glucose/galactose binding protein of *Escherichia coli* (GGBP), as disclosed in MARVIN et al., Proc. Natl. Acad. Sci. USA, 94:4366-4371 (1997); and MARVIN et al., J. Am. Chem. Soc., 120:7-11 (1998), both of which are incorporated by reference herein.

Structural studies of GGBP reveal two domains, the relative positions of which change upon the binding of glucose, as disclosed in CAREAGA et al., Biochem., 34:3048-3055 (1995), which is incorporated by reference herein. Such conformational changes result in spectral changes of environmentally sensitive probes, or changes in the transfer efficiency between donor and acceptor pairs covalently bound to the protein.

U.S. Pat. No. 6,521,446 to HELLINGA, which is incorporated by reference herein, discloses a glucose biosensor comprising a genetically engineered glucose binding protein that includes environmentally sensitive reporter group(s). This document discloses several reporter groups, including osmium(II) bisbipyridyl complexes.

DATTELBAUM et al., Anal. Biochem., 291:89-95 (2001), which is incorporated by reference herein, discloses that labeling a cysteine in position 179 of a glutamine-binding protein with a polarity-sensitive probe, such as acrylodan, results in changes in the fluorescence properties of the probe in response to glutamine. This document discloses that the phase angle was measured at 110 MHz.

TOLOSA et al., Anal. Biochem., 267:114-120 (1999); and LAKOWICZ et. al., Anal. Chem., 70:5115-5121 (1998), both of which are incorporated by reference herein, describe a method in which a labeled glutamine-binding protein is used with an external reference—a long-lived metal-ligand complex—that was added to the solution or applied to the walls of a cuvette. These documents disclose that the combined emission of the labeled protein and the metal-ligand complex allowed for the detection of modulation changes at lower frequencies.

U.S. Pat. No. 6,197,534 to LAKOWICZ et al., which is incorporated by reference herein, discloses engineered proteins for analyte sensing. This document discloses that mutant glucose/galactose binding proteins may have attached fluorophores with widely spaced lifetimes, permitting modulation-based glucose sensing. This document discloses an embodiment in which a long lifetime metal-ligand complex is painted on the outside of a cuvette.

ZHOU et al., Biosens. Bioelectr., 6:445-450 (1991), which is incorporated by reference herein, discloses the immobilization of maltose binding protein (MBP) labeled with IAEDANS. MBP-IAEDANS was immobilized onto PCG by glutaraldehyde coupling, carbodiimide coupling, and diazonium coupling.

WENNER et al., Proc. SPIE, 4252:59-70 (2001), which is incorporated by reference herein, discloses immobilizing phosphate-binding protein (PBP) labeled with N-[2-(1-maleimidyl)ethyl]7-diethylaminocoumarin-3-carboxamide ("MDCC") in sol-gel.

There remains, however, a need for improved proteins, sensors, and methods for characterizing samples.

SUMMARY OF THE INVENTION

Accordingly, the present invention provides proteins, sensors including proteins, and methods of characterizing samples.

In one embodiment, the present invention is directed to a protein sensing molecule that is capable of binding an analyte in a sample. The protein sensing molecule includes a first detectable quality that changes in a concentration dependent manner when the protein sensing molecule is bound to the analyte. The protein sensing molecule also includes a second detectable quality that does not undergo substantial change when the protein sensing molecule is bound to the analyte.

In another embodiment, the present invention is directed to a method for characterizing a sample. The method includes contacting a protein sensing molecule with the sample, the protein sensing molecule being capable of binding an analyte in the sample. The protein sensing molecule includes a first detectable quality that changes in a concentration dependent manner when the protein sensing molecule is bound to the analyte, and a second detectable quality that does not undergo substantial change when the protein sensing molecule is bound to the analyte. The method also includes measuring the detectable qualities of the protein sensing molecule, and analyzing the detectable qualities to characterize the sample.

In still another embodiment, the present invention is directed to a sensor. The sensor includes a protein sensing molecule that is capable of binding an analyte in a sample. The protein sensing molecule includes a first detectable quality that changes in a concentration dependent manner when the protein sensing molecule is bound to the analyte, and a second detectable quality that does not undergo substantial change when the protein sensing molecule is bound to the analyte. The sensor also includes a radiation source for irradiating a sample, and a detector that detects changes in the detectable quality of the first detectable quality and the second detectable quality.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings wherein.

DETAILED DESCRIPTION OF PREFERRED EMBODIMENTS

Definitions

Figure 1:
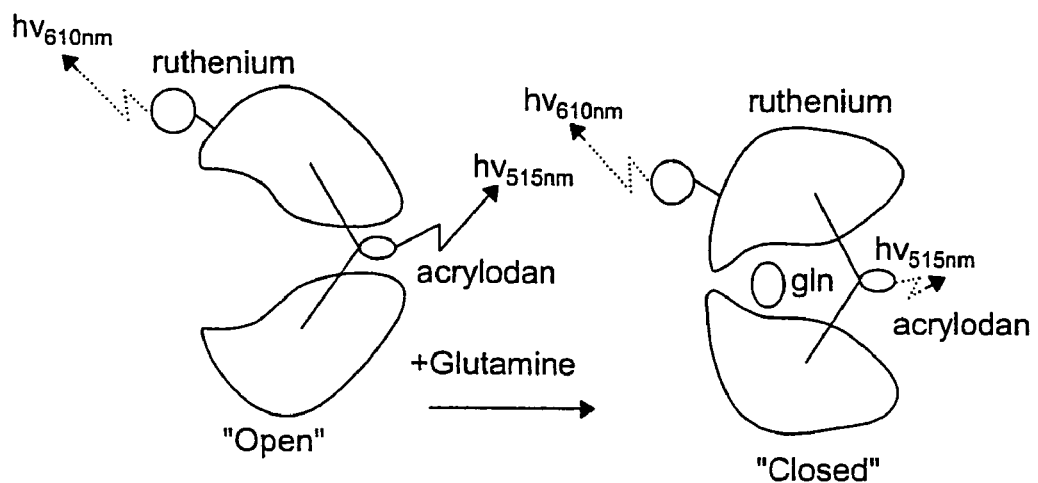
FIG. 1 is a schematic representation of a protein of the present invention, wherein the protein is shown in an open position before analyte binding and in a closed position after analyte binding, i.e., a detectable conformational change.

Unless otherwise stated, a reference to a compound or component includes the compound or component by itself, as well as in combination with other compounds or components, such as mixtures of compounds.

As used herein, the singular forms "a," "an," and "the" include the plural reference unless the context clearly dictates otherwise.

As used herein, the term "protein" includes not only a full-length protein, but also smaller polypeptide fragments that display the desirable binding characteristics described herein. For example, the protein can consist of the analyte-binding site alone, although it is preferred that substantially more of the polypeptide from which the analyte-binding site was derived also forms part of the protein. Thus, it is preferred that those sequences of the polypeptide that are required to maintain the conformation of the binding site also form part of the protein.

Typical proteins include those that bind reversibly to the analyte and display a detectable change. In some embodiments, the protein has a single binding site for the analyte, which minimizes aggregation due to cross-linking and maximizes reversibility. It is also desirable that the protein be stable and easy to purify following cloning and expression. Cooperative binding of the analyte is also desirable, as that effect could increase detectable changes in the physiologically important range of analyte concentrations. It is also preferable that the protein bind the analyte without displaying significant chemical transformation of the analyte.

As used herein, "long-lived" is intended to mean having a fluorescence lifetime of at least about 200 ns. For instance, the labels or metal complex labels of the present invention may have a fluorescence lifetime of at least about 300 ns, at least about 500 ns, at least about 750 ns, or at least about 1000 ns.

As used herein, the term "analyte" refers to any compound that may be able to interact, to any extent, with a protein of the present invention. It will be understood that the term does not imply that a compound is the "natural" substrate for the protein. In some cases, a high specificity protein will limit the number of chemical entities that can bind. In other cases, the use of broad specificity proteins and variants thereof will allow a broad range of different chemical entities to bind.

As used herein, the terms "test analyte" or "known analyte" refer to analytes that have a known structure and/or biological property of interest. In some embodiments of the present invention, a set of test analytes is used to calibrate an array of proteins.

As used herein, the term "sample analyte" refers to an analyte whose identity is, or is suspected to be, previously encountered by a sensor of the present invention. For example, a sensor of the present invention may be used to identify a sample analyte by comparing its binding pattern with the binding patterns of test analytes whose identity has previously been established.

As used herein, the term "candidate analyte" is an analyte that is to be investigated for a desired biological property by comparison of its binding pattern with the binding pattern of test analytes, at least some of which are known to have the biological property in question. In this aspect of the invention, it is not necessary for the sensor to have previously encountered the candidate analyte. For example, the property of the analyte may be inferred by a neural network, multivariate statistical or pattern recognition analysis software associated with the sensor through its learned knowledge of binding profiles common to members of the test analyte set that share the biological property of interest.

As used herein, a "biological solution" includes, but is not limited to, blood, perspiration, and/or ocular or interstitial fluid, and combinations thereof.

As used herein, the term "sugar derivative" means a system in which one or more of the hydroxyl groups on the sugar moiety has been modified (for example acylated), or a system in which one or more of the hydroxyl groups is not present.

As used herein, the term "sugar analog" means a chemical compound that is structurally similar to a sugar but differs slightly. For example, one atom of a sugar may be replaced with an atom of a different element or one functional group of a sugar may be replaced by a different functional group.

As used herein, "matrix" means a three-dimensional environment capable of immobilizing, entrapping, or encapsulating at least one protein for the purpose of measuring a detectable signal from an analyte-protein interaction.

As used herein the term "hydrolytically condensable siloxane" refers to sol-gel precursors having a total of four substituents, at least one, preferably two, and most preferably three or four of the substituents being alkoxy substituents covalently bound to silicone through oxygen and mixtures thereof. In the case of three, two, and one alkoxy substituent precursors, at least one of the remaining substituents preferably is covalently bound to silicone through carbon, and the remaining substituent(s) contain an organic functionality selected from alkyl aryl, amine, amide, thiol, cyano, carboxyl, ester, olefinic, epoxy, silyl, nitro, and halogen.

Particularly Preferred Embodiments

In a first particularly preferred embodiment, the present invention is directed to a protein sensing molecule that is capable of binding an analyte in a sample. The protein sensing molecule includes a first detectable quality that changes in a concentration dependent manner when the protein sensing molecule is bound to the analyte. The protein sensing molecule also includes a second detectable quality that does not undergo substantial change when the protein sensing molecule is bound to the analyte.

In a second particularly preferred embodiment, the present invention is directed to a method for characterizing a sample. The method includes contacting a protein sensing molecule with the sample, wherein the protein sensing molecule is capable of binding an analyte in the sample. The protein sensing molecule includes a first detectable quality that changes in a concentration dependent manner when the protein sensing molecule is bound to the analyte, and a second detectable quality that does not undergo substantial change when the protein sensing molecule is bound to the analyte. The method also includes measuring the detectable qualities of the protein sensing molecule, and analyzing the detectable qualities to characterize the sample.

In a third particularly preferred embodiment, the present invention is directed to a sensor. The sensor includes a protein sensing molecule that is capable of binding an analyte in a sample. The protein sensing molecule comprises a first detectable quality that changes in a concentration dependent manner when the protein sensing molecule is bound to the analyte, and a second detectable quality that does not undergo substantial change when the protein sensing molecule is bound to the analyte. The sensor also includes a radiation source for irradiating a sample, and a detector that detects changes in the detectable quality of the first detectable quality and the second detectable quality.

Protein Sensing Molecules
First Detectable Quality

The protein sensing molecule of the present invention includes a first detectable quality that changes in a concentration dependent manner when the protein sensing molecule is bound to analyte.

The physical characteristics of the first detectable quality are susceptible to change upon analyte binding. In other words, the characteristic is altered, modulated, or otherwise affected by the binding of an analyte. The maximum signal change of the first detectable quality of the proteins of the present invention is not particularly limited as long as the change is significant enough to be detected. For example, the signal change may range from about 5% to about 100%, about 10% to about 80%, about 30% to about 60%, or about 40% to about 50%.

The first detectable quality is preferably a fluorescent label. The change in the physical characteristics of the label is typically detected by optical or electrical means. Preferably, the detection is via optical means.

The first detectable quality may be attached at any appropriate position within the protein, such that the physical characteristics of the label will be changed upon binding of the analyte. Thus, the first detectable quality may be attached within the analyte-binding site, so long as it does not interfere with analyte binding, or the label may be attached outside the analyte-binding site, but in either case is so positioned that analyte binding causes a change in the physical characteristics of the label. Thus, in some embodiments, the first detectable quality is distant from the analyte-binding site, e.g., more than 10 amino acids from the analyte-binding site. In other embodiments, the first detectable quality is near the analyte-binding site, e.g., in or within 10 amino acids of the analyte-binding site.

In sensors involving a plurality of proteins, the label having a detectable quality that is affected by analyte binding may be attached at the same or different sites within the various members of the group. The positioning of the label having a detectable quality that is affected by analyte binding at different sites, for example, in the analyte-binding site of the protein, may have an effect on the specificity/affinity of that protein for analyte binding. By positioning the label having a detectable quality that is affected by analyte binding at differing sites throughout the protein, further variants are effectively created.

The first detectable quality may be attached to the protein using techniques known in the art. The first detectable quality may be covalently or non-covalently bound to the protein. In one example, the first detectable quality may be attached to the protein via a cysteine residue. The cysteine residue may be naturally occurring or may have been introduced.

Suitable location(s) in polypeptide proteins for the introduction of cysteine residues for fluorescent labeling may be chosen by a person skilled in the art, preferably placing them so that they do not interfere with the binding of the analyte. The cysteine residues are preferably placed on or near residues that move and/or change conformation upon analyte binding. In addition or alternatively, such residues are preferably placed at a location that will not interfere with expression/purification/immobilization of the protein. In some embodiments, a cysteine residue is positioned such that exposure to solvent is altered (i.e., increased or decreased) as a consequence of analyte binding. In a highly preferred embodiment of the present invention, each of these preferences is satisfied in the placement of a cysteine residue for reaction with a fluorophore.

If sufficient information is not available to make meaningful choices about the placement of a cysteine residue for fluorophore labeling, a simple trial-and-error approach may be used, e.g., making a number of variants and picking the variant with the cysteine location resulting in the protein with the most suitable characteristics as described herein.

Thus, when the protein binds an analyte, there is a detectable change in a characteristic of the first detectable quality. Preferably, the detectable quality is a detectable spectral change. When, for example, the label is a fluorophore, analyte binding may cause a change in a fluorescent property, e.g., intensity, excited state lifetime, fluorescent decay time (e.g., determined by time domain or frequency domain measurement), excitation or emission wavelength, polarization, fluorescent anisotropy, a spectral shift of the emission spectrum, a change in time-resolved anisotropy decay (e.g., determined by time domain or frequency domain measurement), etc.

Preferably, the label having a detectable quality that is affected by analyte binding is a fluorescent group with excitation and/or emission wavelength in the optical spectrum (350 to 750 nm). More preferably, the label shows an increase in emission intensity and/or shift in emission wavelength.

Examples of fluorescent labels that vary among themselves in excitation and emission maxima are listed in Table 1 of WO 97/28261, which is incorporated by reference herein. These (each followed by [excitation max./emission max.] wavelengths expressed in nanometers) include wild-type Green Fluorescent Protein [395(475)/508] and the cloned mutant of Green Fluorescent Protein variants P4 [383/447], P4-3 [381/445], W7 [433(453)/475(501)], W2 [432(453)/480], S65T [489/511], P4-1 [504(396)/480], S65A [471/504], S65C [479/507], S65L [484/510], Y66F [360/442], Y66W [458/480], Ioc [513/527], W1B [432(453)/476(503)], Emerald [487/508], and Sapphire [395/511]. This list is not exhaustive of fluorescent proteins known in the art; additional examples are found in the Genbank and SwissProt public databases.

Other useful labels include those that display resonance energy transfer (RET). Many such donor-acceptor pairs are known, and include fluorescein to rhodamine, coumarin to fluorescein or rhodamine, etc. Still another class of useful label pairs includes fluorophore-quencher pairs in which the second group is a quencher that decreases the fluorescence intensity of the fluorescent group. Some known quenchers include acrylamide groups, heavy atoms such as iodide and bromate, nitroxide spin labels such as TEMPO, etc.

Alternatively, fluorophores such as fluorescent dyes may be used. Examples of fluorescent dyes include the following non-limiting list of chemical fluorophores provided, together with their emission wavelengths, in Table 1, below.

TABLE 1

| Fluorophore | Excitation (nm) | Emission (nm) | Color |
|---|---|---|---|
| PKH2 | 490 | 504 | Green |
| PKH67 | 490 | 502 | Green |
| Fluoroscein (FITC) | 495 | 525 | Green |
| Hoechst 33258 | 360 | 470 | Blue |
| R-Phycoerythrin (PE) | 488 | 578 | Orange-red |
| Rhodamine (TRITC) | 552 | 570 | Red |
| Quantum Red ™ | 488 | 670 | Red |
| PKH26 | 551 | 567 | Red |
| Texas Red | 596 | 620 | Red |
| Cy3 | 552 | 570 | Red |

A particularly preferred group of labels for use in the present invention is the so-called fluorescent labels. Fluorescent labels are environmentally sensitive, such that changes in, for example, the pH or polarity of the environment, potentially caused by analyte binding to the protein, will have an effect on the properties of the label. Such fluorescent labels are also less sensitive to the non-specific binding background and enable quantitative measurements to be made. Thus, fluorescent labels are capable of reporting the mechanism of binding of an analyte rather than simply being switched on or off by binding of the analyte.

In view of the above, the protein of the present invention may include one or more polarity-sensitive labels. The polarity-sensitive label(s) have a detectable quality that is affected by analyte binding at the analyte-binding site. Examples of polarity-sensitive labels include, but are not limited to, dansyl labels, ananilinonapthalene labels, deproxyl labels, phthalamide labels, amino pH phthalamide labels, and labels comparable to Prodan, Lordan, or Acrylodan. Such labels are sensitive to the polarity of the local environment and are known to those of skill in the art.

In one embodiment, analyte binding causes one or more of the polarity-sensitive label(s) to be shielded. In another embodiment, analyte binding causes one or more of the polarity-sensitive label(s) to be unshielded.

When the first detectable quality is a fluorescent label, it is generally preferred that the label has at least some and preferably all of the following properties: (1) low molecular weight, for example, from about 150 Da to about 500 Da; (2) conjugateability in a site-specific manner to thiol groups that have been introduced into or are naturally occurring in the target area of the protein; (3) enhanced fluorescence over that observed in free solution when conjugated with thiol groups that are buried or unsolvated, for example cysteine groups present or introduced in the protein of the present invention; and (4) exhibits a detectable shift in fluorescence emission spectra on binding of analyte to the protein.

Examples of fluorescent labels suitable for use as labels in the present invention include, but are not limited to, those shown in Table 2, below.

TABLE 2

| Fluorescent Label | Excitation (nm) | Emission (nm) |
|---|---|---|
| Iodoacetylnitrobenzoxadiazole | 482 | 520 |
| Acrylodans | 360 | 430-550 |
| Iodoacetamidobenzoxadiazole | 482 | 525 |

Further fluorescent labels suitable for use include, but are not limited to, coumarins, anilino-naphthalene sulfonate (ANS), anilino-naphthalene sulfonate iodoacetamide (IAANS), anilino-naphthalene sulfonate maleimide (MIANS), N-(4,6-dimethylamino-2-benzofuranyl)phenyl maleimide (DAFP), and 5-{([(2-iodoacetyl)amino]ethyl)amino}naphthalen-e-1-sulfonic acid (IAEDANS).

Although the acrylodan dyes generally react with thiol groups more slowly than do the IAANS and MIANS compounds, acrylodan dyes form strong thioether bonds that are typically stable under most reactive conditions. The fluorescence emission peak and intensity of these adducts are particularly sensitive to conformational changes or analyte binding.

Most acrylodan dyes suitable for use as a label in the present invention have their longest-wavelength absorption peaks at less than about 400 nm. Typically, these dyes exhibit blue fluorescence and have weak absorption, with extinction coefficients often below 20,000 $cm^{-1}M^{-1}$. Photostability of UT light-excitable dyes is typically is less than that of visible light-excitable dyes. The strong dependence of the emission spectra and quantum yields of several of the dyes makes them useful for studying analyte binding to receptors. The spectra of certain dyes tend to be particularly sensitive to analyte and metal binding, protein association and chaotropic reagents. When protein conjugates of these dyes are denatured or undergo a change in conformation, a decrease in fluorescence intensity and a shift in emission to longer wavelengths are often observed.

A further fluorescent label suitable for use as a label in the present invention is IANBD, i.e., (((2-(iodoacethoxy)ethyl)methyl)amino)-7-nitrobenz-2-oxa-1,3-diazole. This compound contains donor-acceptor electron pairs and can form a twisted intramolecular charge transfer (TICT) excited state, both of which ensure that excited state relaxation is sensitive to rotational freedom and/or solvation. The intensity of fluorescence emission of IANBD is highly sensitive to changes in the solvation level of the fluorophore. Upon analyte binding to conjugated amino acid residues, the label's localized electronic environment is disturbed resulting in a quenching or enhancement of fluorescence being seen. The nature of this change is reflective of both the structure of the bound analyte, the nature of the interaction (hydrophobic, van-der Waal's, dipolar, etc.), and the nature of the assay medium (pH, ionic strength).

Other suitable fluorescent labels for use in the present invention include IAANS and MIANS. To develop appreciable fluorescence, both the reactive IAANS and MIANS must be reacted with thiols that are located in hydrophobic sites. Often, however, buried unsolvated thiol residues are exceptionally reactive, allowing these sites to be selectively modified by these reagents. The environmentally sensitive fluorescence properties of the protein conjugates of MIANS and IAANS are similar to those of IANBD. The fluorescence intensity, and to a lesser extent the emission wavelengths, of the conjugates tends to be very sensitive to substrate binding, folding and unfolding of the protein, and changes in local polarity. Like most other maleimides, MIANS is essentially non-fluorescent until it has reacted with a thiol.

IAEDANS is another fluorescent label that may be used in the present invention. The fluorescence of IAEDANS is quite dependent on environment, although much less so than that of IAANS and MIANS conjugates. Conjugates of IAEDANS frequently respond to analyte binding by undergoing spectral shifts and changes in fluorescence intensity that are determined by the degree of aqueous solvation. Advantages of this reagent include high water solubility above pH 4 and a relatively long fluorescence lifetime (sometimes >20 nanoseconds, although commonly 10-15 nanoseconds). In addition, because it has a large Stokes shift and an emission that overlaps well with the absorption of fluoroscein, Alexa Fluor 488, Oregon Green dyes and BODIPY FL dyes, IAEDANS is an excellent reagent for (FRET) measurements of proximity up to about 60 Å.

The most preferred fluorescent labels for use as labels in the present invention are anilino-naphthalene sulfonate (ANS) and acrylodans.

Although the use of fluorescent labels is preferred, other detectable characteristics may be used. For example, electrochemical reporter groups could be used wherein an alteration in the environment of the reporter gives rise to a change in the redox state thereof. Such a change may be detected, for example, by use of an electrode.

Furthermore, other spectroscopically detectable labels, for example labels detectable by NMR (nuclear magnetic resonance), may be used. Still further, radioactive labels may be used.

Second Detectable Quality

The protein sensing molecule of the present invention also includes a second detectable quality that does not undergo substantial change when the protein sensing molecule is bound to the analyte.

The second detectable quality typically acts as a reference. Thus, the emission intensity of the second detectable quality is substantially unaffected by analyte binding. For instance, the signal change may be less than about 5%, less than about 2%, less than about 1%, or less than about 0.5%.

For example, the second detectable quality may be one or more of those labels listed above as first detectable qualities, as long as the label fulfills the criteria for second detectable qualities.

In some embodiments, the second detectable quality is positioned on the protein such that analyte binding at the analyte-binding site does not shield the second detectable quality.

In some embodiments, the second detectable quality comprises one or more metal complex labels, such as long-lived metal complex labels, having a detectable quality. In certain embodiments, the metal complex(es) comprise a fluorophore. Examples of suitable long-lived metal complex fluorophores include palladium, platinum, ruthenium, and osmium complexes, such as $[Ru(bpy)_3]^{2+}$, $[Ru(Ph_2phen)_3]^{2+}$, $[Ru(bpy)_2(dcbpy)]^{2+}$, and $[Ru(bpy)_2(phen-ITC)]^{2+}$, where bpy is 2,2'-bipyridine, phen is 1,10-phenanthroline, dcbpy is 4,4'-dicarboxy-2,2'-bipyridine, and ITC is isothiocyanate.

In preferred embodiments, one or more long-lived metal complex(es) is attached at a position where minimal environmental changes are expected. For example, the complex(es) may be attached at the N-terminal or C-terminal of the protein.

FIG. 1 shows an exemplary protein in which acrylodan, a first detectable quality, is covalently attached to a cysteine mutation on the opposite side of a glutamine-binding site. In the "open" or glutamine-free conformation, the protein shields the acrylodan. In contrast, in the "closed" or glutamine-bound conformation, the acrylodan is exposed to solvent. This exposure to solvent results in a decrease in the acrylodan intensity. In both cases, a second detectable quality, i.e., a ruthenium label, is unaffected by the conformational changes thereby serving as a label.

Analyte-Binding Site

The protein of the present invention may include one or more analyte-binding site(s). Depending on the purpose of the protein, the analyte-binding site may have high specificity or may have broad specificity.

For example, high specificity analyte-binding sites are useful in sensors for determining the presence or concentration of analytes. The high specificity allows determination of the presence or concentration of specific analytes with minimal interference from similar analytes.

In this regard, the protein may, e.g., have a binding constant for an analyte that ranges from about 0.1 µM to about 30 mM, such as about 0.2 µM to about 20 mM, about 0.6 µM to about 10 mM, or about 1 µM to about 1 mM. For example, a glutamine-binding protein (GlnBP) in accordance with the present invention has a binding affinity ($K_d$) of 0.2 µM for glutamine. As another example, a glucose binding-protein (GBP) of the present invention has a binding affinity of about 0.8 µM for glucose. In yet another example, a GBP of the present invention has a binding affinity of about 0.4-1.4 µM for glucose.

Thus, the protein may have a binding affinity in the micromolar range. In some embodiments, the protein has micromolar sensitivity for both glucose and galactose. Thus, the protein may be used, e.g., for monitoring either glucose or galactose in the absence of the other.

Broad specificity analyte-binding sites are useful in devices, such as detector arrays, for characterizing analytes. Proteins having broad specificity may be described as being promiscuous. Thus, the protein is capable of binding to a wide variety of different analytes. The binding affinity of the protein for different analytes may vary. Preferably, the proteins are capable of binding a broad range of structurally diverse analytes. Broad specificity or promiscuity may also be understood to relate to the structural determinants of the analyte(s) to which the protein binds. Although not every protein in a detector array need have broad specificity or be promiscuous, it is preferred that substantially all of the proteins possess such broad specificity/promiscuity.

A broad specificity/promiscuous protein preferably binds a number of analytes, which analytes may apparently lack a common structural determinant, such as conserved functional group(s) or particular size or shape of molecule. Shared features by contrast, usually define classes or types of molecules (analytes) binding to highly specific proteins.

Therefore, the choice of protein for the present invention will be influenced to a certain extent by the analyte. The proteins of the present invention are typically chosen for their ability to bind analytes of low molecular weight. Typically, the molecular weight of analytes used in accordance with the present invention range from about 32 Da to about 600 Da, such as about 50 Da to about 500 Da, or about 100 Da to about 400 Da. These molecular weight ranges include many biologically important molecules, including small molecule drugs.

Examples of analytes include analytes whose identity is known and analytes whose identity is unknown. Examples of analytes include, but are not limited to, amino acids (e.g., glutamine, glutamate), sugars (e.g., glucose, galactose, maltose), ions (e.g., calcium, phosphate, sulfate), metabolites (e.g., lactate), toxins (e.g., hemolysin), drug candidates, and derivatives thereof.

For some embodiments, e.g., involving drug screening, candidate analytes may be obtained from commercially available libraries of compounds, or generated de novo using, for example combinatorial chemistry (see, for example, *A Practical Guide to Combinatorial Chemistry*, A. W. Czarnik & S. H. DeWitt, American Chem. Soc. (1997); and *Combinatorial Chemistry*, N. K. Terrett, OUP (1998), both of which are incorporated by reference herein). Commercially available libraries of compounds are available from, for example, Sigma-Aldrich-Fluka, Chemical Diversity Incorporated, and Tripos.

Examples of low molecular weight analytes that can be recognized using, e.g., a detector array of the present invention include, but are not limited to, classes of drug, such as angiotensin converting enzyme inhibitors, beta-adrenergic inhibitors and non-steroidal anti-inflammatory agents; general classes and functional derivatives of organic molecules, such as aromatic and aliphatic alcohols, aldehydes, and ketones; natural products such as terpenes and simple sugars.

In view of the above, exemplary polypeptides having suitable analyte-binding sites include, but are not limited to, glutamine-binding protein (GlnBP), glucose-binding protein (GBP) (also known as galactose/glucose-binding protein), maltose-binding proteins, phosphate-binding proteins, arabinose-binding proteins, mammalian or insect olfactory binding proteins (e.g., human olfactory binding protein (hOBP), bovine olfactory binding protein (hOBP), and porcine olfactory binding protein (pOBP)), membrane-bound proteins, chaperone proteins (e.g. Gα15 and Gα16), PXR receptor, taste receptors, DNA binding proteins, serum albumin (human and bovine), cytochrome P450's, P-glycoprotein, major urinary protein, and others. Particularly preferred polypeptides include GlnBP and GBP.

Since GBP has a single analyte-binding site and lacks polymeric acceptors, there is a complete reversibility upon removal of glucose. Like similar transport proteins from other bacteria, GBP is highly specific for binding glucose and/or galactose. The apparent binding affinity of GBP for sugars other than glucose or galactose is typically 100-1000 fold weaker. In view of the high affinity for glucose, sensors based on GBP can be used on small volumes of blood or interstitial fluid.

Hexokinase and glucokinase may also be used in the present invention to detect glucose. For use in detecting blood glucose levels, the hexokinase or glucokinase would have to have a lower affinity constant for glucose. This could be accomplished with mutants of hexokinase, for example, that have a lower affinity for glucose, or possibly with mutants of GBP engineered to have a lower glucose binding constant.

Combinations of polypeptide and non-polypeptide molecules may be employed as sensors in the present invention, such as maltose binding protein complexed with cyclodextrin or other host molecules. This combination is particularly advantageous in the study of non-steroidal anti-inflammatory compounds as analytes.

Although the analyte-binding site need not be specifically characterized in terms of its ammo acids, it is preferred that at least the location of the analyte-binding site within the polypeptide is known, and it is more preferred that at least some information on amino acids with respect to the analyte-binding site is known. Determination of the location of the analyte-binding site within a polypeptide may be made using techniques known in the art, e.g., X-ray crystallography. Determination of the specific ammo acids in an analyte-binding site may likewise be made using techniques known in the art.

Additional Protein Characteristics

In some embodiments, the protein comprises a naturally occurring protein that has been modified. The modification may serve one or more purposes. For example, a protein may be modified in order to adjust its binding constant with respect to the analyte; to change the long-term stability of the protein; to conjugate the protein to a polymer; to provide binding sites for detectable labels; etc.

Examples of modified proteins include, but are not limited to, modified glutamine-binding protein, modified glucose-binding protein, modified hexokinase, and modified glucokinase.

For example, the protein may be modified by substituting at least one cysteine residue therein. Exemplary mutations of the GBP protein include, but are not limited to, one or more of the following: a cysteine substituted for a lysine at position 11 (K11C); a cysteine substituted for aspartic acid at position 14 (B14C); a cysteine substituted for valine at position 19 (V19C); a cysteine substituted for asparagine at position 43 (N43C); a cysteine substituted for a glycine at position 74 (G74C); a cysteine substituted for a tyrosine at position 107 (Y107C); a cysteine substituted for threonine at position 110 (T110C); a cysteine substituted for serine at position 112 (S112C); a double mutant including a cysteine substituted for a serine at position 112 and serine substituted for an leucine at position 238 (S112C/L238S); a cysteine substituted for a lysine at position 113 (K113C); a cysteine substituted for a lysine at position 137 (K137C); a cysteine substituted for glutamic acid at position 149 (E149C); a double mutant including a cysteine substituted for an glutamic acid at position 149 and a serine substituted for leucine at position 238 (E149C/L238S); a double mutant comprising a cysteine substituted for histidine at position 152 and a cysteine substituted for methionine at position 182 (H152C/M182C); a double mutant including a serine substituted for an alanine at position 213 and a cysteine substituted for a histidine at position 152 (H152C/A213S); a cysteine substituted for an methionine at position 182 (I82C); a cysteine substituted for an alanine at position 213 (A213C); a double mutant including a cysteine substituted for an alanine at position 213 and a cysteine substituted for a leucine at position 238 (A213C/L238C), a cysteine substituted for an methionine at position 216 (M216C); a cysteine substituted for aspartic acid at position 236 (D236C); a cysteine substituted for a leucine at position 238 (L238C); a cysteine substituted for an aspartic acid at position 287 (D287C); a cysteine substituted for an arginine at position 292 (R292C); a cysteine substituted for a valine at position 296 (V296C); a triple mutant including a cysteine substituted for a glutamic acid at position 149, an alanine substituted for a serine at position 213, and a serine substituted for leucine at position 238 (E149C/A213S/L238S); a triple mutant including a cysteine substituted for an glutamic acid at position 149, an arginine substituted for an alanine at position 213 and a serine substituted for leucine at position 238 (E149C/A213R/L238S); a quadruple mutant including a serine at position 1, a cysteine at position 149, an arginine at position 213 and a serine at position 238 (A1S/E149C/A213R/L238S); a quadruple mutant including a serine at position 1, a cysteine at position 149, a serine at position 213, and a serine at position 238 (A1S/E149C/A213S/L238S); and a quadruple mutant including a cysteine at position 149, a cysteine at position 182, a cysteine at position 213, and a serine at position 238 (E149C/M182C/A213C/L238S).

The amino acid residue numbers refer to the published sequence of E. coli having 309 residues or the corresponding amino acid residue in any substantially homologous sequence from an alternative source (e.g., glucose binding proteins from *Citrobacter freundii* or *Salmonella typhimurium*, sequence accession numbers P23925 and P23905, respectively).

In a preferred embodiment, the protein is a modified glutamine-binding protein that contains a cysteine residue at position 179, which cysteine residue is attached to a polarity-sensitive label. In another embodiment, the protein is a modified glutamine-binding protein that contains a cysteine residue at position 209, which cysteine residue is attached to a polarity-sensitive label. In one embodiment, an E. coli glutamine-binding protein is useful in reagentless fluorescence sensing of glutamine in a manner that is sensitive in the submicromolar range.

In another embodiment, an S179C variant of GlnBP is labeled at the —SH and N-terminal positions with acrylodan and ruthenium bis-(2,2'-bipyridyl)-1,10-phenanthroline-9-isothiocyanate, respectively. In this embodiment, the acrylodan emission is quenched in the presence of glutamine while the ruthenium acts as a nonresponsive long-lived reference.

When GBP is the protein, it is especially useful to genetically engineer mutant GBP's with selectively placed cysteines, such that thiol-reactive molecules may be covalently bound to the protein. Sites may be selected based on the structure of the protein so that, for example, glucose binding will cause spectral changes for GBP labeled with environmentally sensitive labels. In some embodiments, the conformational change of GBP causes interactions between fluorophores bound to separate domains of the protein that move relative to each other in response to glucose binding. Additionally, mutant GBP's may have attached fluorophores with widely spaced lifetimes, permitting modulation-based or ratiometric-based glucose sensing.

For example, mutant GBP's may be created by replacing one amino acid residue with cysteine at position 26, or replacing two amino acid residues with cysteines at positions 26 and 182. These positions are useful because they are close to a hinge region between two domains of GBP. Site 26 is exposed by conformational change of the protein upon glucose binding, thereby changing the environment of a label bound at that site.

In another embodiment, a dual-emitting E. coli glucose binding protein (GBP) was prepared by labeling a cysteine mutation at position 255 (L255C mutant) and the N-terminal with the long-lived environment-insensitive ruthenium bis(2,2'-bipyridl)-1,10-phenanthroline-9-isothiocyanate. In this embodiment, upon glucose binding, the polarity-sensitive acrylodan is exposed to the solvent, resulting in a decrease in fluorescence intensity.

In general, the further the distance between the first and second detectable qualities, the less likely that the first detectable quality will interact with the second detectable quality. For example, the fluorescence intensity of ANS on the Q26C mutant is close to the N-terminal of the protein. As such, its fluorescence intensity was almost totally quenched when ruthenium was attached to the N-terminal. The position at 255 is about 15 Å further away from the N-terminal. In this regard, for the L255C mutant, calculations of the fluorescence energy-transfer efficiency between acrylodan and ruthenium gave an approximate distance of 25 Å between the two fluorophores, consistent with X-ray crystallographic data. Even at this distance, quenching of the acrylodan was observed. Nevertheless, this quenching, which is attributed to FRET between acrylodan and ruthenium, is advantageous in that the ruthenium signal was enhanced to allow ratiometric measurements, as discussed in more detail below.

The enthalpy change for the L255C mutant, as calculated from the apparent binding constants, was about 43.1 kJ/mol.

In some cases, the positioning of the label depends on the type of label. For example, when ANS is attached to site 26 of GBP, the protein is functional. In contrast, when acrylodan is attached at position 26 of GBP, it is nonresponsive.

Preferably, the proteins are proteins/polypeptides or fragments thereof that are of small size. Typically, the protein is less than about 200 kDa in weight, such as less than about 100 kDa or less than about 50 kDa in weight.

In preferred embodiments, the protein of the present invention is not an enzyme. Thus, it does not consume analyte or require other "reagents" for its activity. In other embodiments, the protein is an enzyme.

In several preferred embodiments, the protein of the present invention is stable. For example, it is known that the protein may be used after about 1 month, after about 2 months, after about 4 months, or after about 5 months, after the protein is made. It is expected that the protein may be used after longer time periods, such as after about 6 months, after about 9 months, or after about 1 year, after the protein is made. In this regard, prior to use, the protein may be stored at reduced temperature, such as at less than room temperature, less than about 20° C., or less than 10° C., such as at 4° C. Suitable storage temperatures can be determined empirically by one skilled in the art.

The binding of the analyte is quick and reversible in solution, but the dissociation equilibrium and mass transfer resistance for encapsulated proteins can delay the response time to several minutes and the recovery to hours. Thus, maximizing material transfer area will reduce response and recovery times. Simulated results show that using dialysis tubing with a diameter of 1 mm or less is possible to reduce the recovery time to less than 30 minutes. The dissociation equilibrium of the proteins may also be optimized to reduce response and recovery time.

Thus, in some embodiments, the protein of the present invention has a fast response time. For instance, the response time of the protein may be less than about 5 minutes, less than about 2 minutes, less than about 1 minute, less than about 30 seconds, less than about 15 seconds, less than about 10 seconds, or less than about 5 seconds.

In view of the reversibility of the binding, in some embodiments, the recovery time of the protein of the present invention is relatively fast. For example, the recovery time of the protein may be less than about 2 hours, less than about 1 hour, less than about 50 minutes, less than about 40 minutes, less than about 30 minutes, or less than about 20 minutes.

Methods of Making Proteins

The proteins of the present invention may be made by any of the various methods and techniques known to those skilled in the art.

In some embodiments, the proteins are proteins/polypeptides or fragments thereof that can be expressed (typically these are readily over-expressed) in a suitable host organism, such as a microorganism, e.g., *E. coli*. This is a standard procedure known to those skilled in the art. Briefly, nucleic acid encoding the polypeptide is cloned into an expression vector and this expression vector is transformed into a host strain of *E. coli* for protein expression. Expression is induced, and preferably proteins/polypeptides or fragments thereof suitable for use as proteins of the present invention are highly expressed, and preferably readily extracted or purified. Less preferred are polypeptides that form insoluble inclusion bodies on expression and which require alternative extraction techniques and in vitro refolding.

From the standpoint of production, the proteins of the present invention can be generated cheaply. For example, they may be preferentially expressed in the periplasm of an *E. coli* host at >80% of the total protein. The only postfermentation step required is to extract the periplasmic fluid by chloroform extraction. In some embodiments, no further purification is necessary because the lack of cysteine-containing proteins in the periplasm allows for the selective labeling of the protein by, e.g., acrylodan. In some embodiments, since acrylodan is responsible for the glutamine-induced signal transduction and not ruthenium, labeling of the other proteins by ruthenium in the mixture does not affect the selectively of the sensor for glutamine.

As an alternative to genetically engineering GBP, donor and acceptor dyes may be attached by making a fusion protein. Therefore, for the double cysteine mutant, labeled for example with a donor-acceptor pair, glucose binding causes changes in the transfer efficiency. For example, this invention includes GBP glucose sensors that are fusion proteins with green fluorescent protein that, by changes in energy transfer efficiency on glucose binding, can measure glucose.

Embodiments involving detection arrays often include proteins and variants thereof. A protein variant may be derived from a starting protein and differs from the starting protein in its binding specificity and/or affinity. Variants may be made by techniques known in the art. For example, variants may be made in accordance with the techniques disclosed in U.S. Published Application No. 20020168692 to CASS.

Devices

The proteins of the present invention may be used in various sensors known to those skilled in the art.

In some embodiments, the sensor includes a protein sensing molecule that is capable of binding an analyte in a sample. The protein sensing molecule includes a first detectable quality that changes in a concentration dependent manner when the protein sensing molecule is bound to the analyte, and a second detectable quality that does not undergo substantial change when the protein sensing molecule is bound to the analyte. The sensor also includes a radiation source for irradiating a sample, and a detector that detects changes in the detectable quality of the first detectable quality and the second detectable quality.

In one embodiment, the present invention is directed to a sensor that includes a, protein comprising an analyte-binding site, a first detectable quality having a detectable quality that is affected by analyte binding at the analyte-binding site, and a second detectable quality having a detectable quality that is substantially unaffected by analyte binding at the analyte-binding site. The sensor also includes a radiation source for irradiating a sample. The sensor additionally includes a detector that detects changes in the detectable quality of the first and second detectable qualities.

In another embodiment, the present invention is directed to a sensor that includes a protein comprising an analyte-binding site, a polarity-sensitive label having a detectable quality that is affected by analyte binding at the analyte-binding site, and a long-lived metal complex label having a detectable quality. The sensor also includes a radiation source for irradiating the sample. The sensor further includes a detector that detects changes in the detectable quality of the polarity-sensitive label and the long-lived metal complex label.

In preferred embodiments, the sensor detects emission from both the first and second detectable qualities. The dual emission of the protein of the present invention presents several possible instrumentation designs. For example, steady-state measurements of the emission at two wavelengths with well-chosen emission filters are an improvement from simple intensity measurements at a single wavelength. In some embodiments, the presence of the long-lived metal complex permits lifetime-based modulation sensing at lower frequencies, as discussed in more detail below.

Although the soluble binding proteins have complete freedom of movement in solution, and thereby exhibit their maximum activity, these proteins may be used repeatedly or continuously after immobilization. Immobilization of proteins is known in the art. See, e.g., U.S. Pat. No. 6,596,545 to WAGNER et al.; U.S. Published Application No. 20020168295 to CUNNINGHAM et al.; and U.S. Published Application No. 20030153026 to ALARCON et al., which are incorporated by reference herein.

Immobilization of the protein onto a support may be performed so that the protein will not be washed away by rinsing procedures, and so that its binding to the analyte in a sample is unimpeded by the support surface. Several different types of surface chemistry strategies have been implemented for covalent attachment of proteins to, for example, glass for use in various types of microarrays and sensors. These same methods can be readily adapted to the sensor of the present invention.

Surface preparation of a support so that it contains the correct functional groups for binding one or more specific binding substances is a preferable part of the sensor manufacturing process.

One or more specific proteins can be attached to a support surface by physical adsorption (i.e., without the use of chemical linkers) or by chemical binding (i.e., with the use of chemical linkers). Chemical binding can generate stronger attachment of proteins on a support surface and provide defined orientation and conformation of the surface-bound molecules.

Thus, the proteins may be immobilized on a solid phase support, e.g., by non-specific adsorption, covalent attachment, or specific capture using an immobilized capture reagent that binds, preferably specifically, the protein. Immobilization may be accomplished by using proteins that are labeled with binding species that form binding pairs with immobilized capture reagents. Optionally, the protein is immobilized on a solid phase, the solid phase is washed and the protein is analyzed; the wash step allows for the rapid purification of the protein from other, potentially interfering components.

Examples of chemical binding of proteins to a sensor of the invention include, but are not limited to, amine activation, aldehyde activation, and nickel activation. These surfaces can be used to attach several different types of chemical linkers to a support surface. While an amine binds proteins directly, without an additional linker, a nickel surface can be used to bind molecules that have an incorporated histidine ("his") tag. Detection of "his-tagged" molecules with a nickel-activated surface is known in the art WHITESIDES, Anal. Chem., 68:490 (1996), which is incorporated by reference herein).

Immobilization, however, may reduce the maximum signal change. While not wishing to be bound by theory, it is believed that the restricted mobility upon immobilization, which limits the conformational change that is necessary for a binding protein to function, is the major reason for this low binding affinity. Among the principal methods for biological immobilization-adsorption, covalent binding, crosslinking, entrapment, and encapsulation-encapsulation is the method that least interferes with the binding process. So it seems to be the best possible method for the immobilization of the proteins.

In one aspect of the present invention, the sensor is used for analyte sensing in vivo. In this aspect, the biosensor is encapsulated into a matrix that may then be used as an implantable device. The matrix may be any desirable form or shape including one or more of disk, cylinder, patch, nanoparticle, microsphere, porous polymer, open cell foam, providing it is permeable to analyte. The matrix additionally prevents leaching of the sensor. The matrix permits light from optical sources or any other interrogating light to or from the detectable qualities to pass through the sensor. When used in an in vivo application, the sensor will be exposed to a substantially physiological range of analyte and determination or detection of a change in analyte concentration would be desired, whereas the determination or detection includes continuous, programmed, and episodic detection means. Thus, the envisaged in vivo sensor of the present invention comprises at least one protein in an analyte permeable entrapping or encapsulating matrix such that the protein provides a detectable and reversible signal when the protein is exposed to varying analyte concentrations, and the detectable and reversible signal can be related to the concentration of the analyte. The implantable sensors may, in some embodiments, be implanted into or below the skin of a mammal's epidermal-dermal junction to interact with the interstitial fluid, tissue, or other biological fluids. Information from the implant to the patient may be provided, for example, by telemetry, visual, audio, or, other means known in the art.

Preferably, the matrix is prepared from biocompatible materials or incorporates materials capable of minimizing adverse reactions with the body. Adverse reactions for implants include, inflammation, protein fouling, tissue necrosis, immune response, and leaching of toxic materials. Such materials or treatments are known and practiced in the art, for example, as taught by QUINN et al., Biomaterials, 16(5):389-396 (1995); and QUINN et al., Biomaterials, 18(24):1665-1670 (1997), which are incorporated by reference herein.

The sensor may be encapsulated into a matrix derived substantially from a hydrogel. The polymer portion of the hydrogel may contain functionality that is suitable for hydrogen bonding or covalent coupling (e.g., hydroxyl groups, amino groups, ether linkages, carboxylic acids and esters, and the like) to the protein.

Numerous hydrogels may be used in the present invention. The hydrogels may be, for example, polysaccharides such as agarose, dextran, carrageenan, alginic acid, starch, cellulose, or derivatives of these such as, e.g., carboxymethyl derivatives, or water-swellable organic polymers such as, e.g., polyvinyl alcohol, polyacrylic acid, polyacrylamide, polyethylene glycol, copolymers of styrene and maleic anhydride, copolymers of vinyl ether and maleic anhydride, and derivatives thereof. Derivatives providing for covalently crosslinked networks are preferred. Synthesis of and medical applications of hydrogels comprising polypeptides, have been described by a number of researchers. (See, e.g., *Biosensors Fundamentals and Applications*, Oxford University Press (1988), which is incorporated herein by reference). An exemplary hydrogel matrix derived from a water-soluble, UV crosslinkable polymer comprises poly(vinyl alcohol), N-methyl-4(4'formylstyryl)pyridinium methosulfate acetal (CAS Reg. No. [107845 0]; available from PolyScience Warrington, Pa.).

In one embodiment of the encapsulation process, one or more hydrogels in water are added to the protein in an aqueous buffer solution having a pH in the range of about 4 to about 10 depending on the protein. Subsequent curing of the matrix, for example, crosslinking, provides physical form. Using this technique and a known fabrication process (e.g., block casting, reverse emulsion polymerization, screen or contact printing, fluid-bed coating, and dip or spin coating) one can obtain matrices in various configurations (e.g., granulates, nanoparticles, microparticles, monoliths, and thick and thin films) suitable for in vitro and in vivo use.

The matrix may, in one embodiment, be comprised of modified sol-gels. Modified sol-gels include at least partially cured (or gelled) preparations comprised of permeable metal oxide glass structures containing in addition to the sol-gel precursor materials, preferably one or more organic components which hydrolytically condense along with the sol-gel precursor such that the resultant sol-gel matrix imparts properties suitable for, by example, implantation. Suitable properties include low volume shrinkage over time, resistance to cracking and other physical defects, maintenance of protein function, and compatibility with the protein and/or detectable characteristic, and compatibility with the animal or subject to which it may be implanted. Suitable organic materials include polyols such as glycerol, ethylene glycol, propylene glycol, polyethylene glycol, and the like, for example, as taught by GILL et al., J. Am. Chem. Soc., 120(34):8587-8598 (1998), which is incorporated by reference herein.

Optimization of sol-gel precursor, organic component, and protein solution materials may be expected for any given protein/detectable characteristic pair. Such optimization may provide for unexpected enhanced signal, shifted binding constants; improved physical performance attributes of the matrix, and combinations thereof relative to that of other matrices or aqueous solutions thereof. Optimization of performance attributes of the protein/detectable characteristic pair and functional performance attributes of the encapsulating matrix may be achieved, for example, by way of combinatorial methods or other statistical design methods known in the art.

Sol-gel matrices useful for the present invention include material prepared by known sol-gel methods and include inorganic material, organic material, or mixed organic/inorganic material. The materials used to produce the sol-gel can include, but are not limited to, aluminates, aluminosilicates, and titanates. These materials may be augmented with the organically modified silicates (ormosils), and functionalized siloxanes, for imparting and manipulating hydrophilicity and hydrophobicity, to provide ionic charge, covalent attachment of protein, and the like.

In one embodiment of the encapsulation process, one or more of hydrolytically condensable siloxane is hydrolyzed in water, either spontaneously or under acid or base catalysis to form derivatives with an organic polyol component present in a molar amount relative to the hydrolytically condensable siloxane of about 10:1 to about 1:10, such as about 5:1 to about 1:5, or about 1:1. To this mixture, prior to final gellation, is added the protein in an aqueous buffer solution having a pH in the range of about 4 to about 10 depending on the protein. At least partial condensation reactions give rise to the final matrices.

In another embodiment, the hydrolytically condensable siloxane hydrolyzed in water, either spontaneously or under acid or base catalysis to form derivatives with the organic polyol, is mixed with a water-soluble polymer component. Suitable water-soluble polymers include polyvinyl alcohol (PVA), poly-(maleic acid co-olefin) sodium salt (PMSA), poly-(vinylsulfonic acid) sodium salt (PVSA), and polyvinyl pyrrolidone (PVP). Poly-(maleic acid co-olefin) includes copolymers of maleic anhydride with styrene, vinyl ether, and C1-C8 olefins and salts thereof, for example, sodium, potassium, ammonium, tetraalkylammonium, and the like. Preferably, the water-soluble polymer component is from 0 to about 30% by weight of the sol-gel composition.

In another embodiment, the hydrolytically condensable siloxane hydrolyzed in water, either spontaneously or under acid or base catalysis to form derivatives with the organic polyol, is mixed with one or more functionalized silicone additives (FSA) in amounts from 0 to about 0.6 mole ratio to hydrolytically condensable siloxane. Exemplary FSA's include alkyl derivatives: for example, methyltrirethoxysilane (MTMOS); amine derivatives: for example, 3-aminopropyl triethoxysilane (ATEOS); and bis silane derivatives: for example, (bis(3-methylditmethoxysilil)propyl) polypropylene oxide (BIS).

In another embodiment, both the water-soluble polymer component and the functionalized silicone additive are mixed together with the hydrolytically condensable siloxane hydrolyzed in water, either spontaneously, or under acid or base catalysis to form derivatives with the organic polyol, to provide for a matrix suitable for entrapment or encapsulation of the protein. Using the aforementioned sol-gel technique and a known fabrication process (e.g., block casting, reverse emulsion polymerization, screen or contact printing, fluid bed coating, and dip or spin coating) one can obtain aerogel or xerogel-matrices in various configurations (e.g., granulates, nanoparticles, microparticles, monoliths, and thick and thin films) suitable for use in vitro and in vivo.

In another embodiment the matrix may be formed from one or more dialysis membranes. The dialysis membranes can be constructed to physically encapsulate or entrap the protein. Covalent attachment to the membrane is considered within the scope of the invention. The membrane should be chosen based on molecular weight cut-off such that analytes of interest can readily permeate the membrane whilst high molecular weight materials would be restricted from entering, or in the case of the proteins, leaving the membrane matrix. The molecular weight cut-off required would be such as to meet the aforementioned requirement and is within the skill of one familiar with this art. Typically, membranes having molecular weight cut-off between about 1000 to about 25,000 Daltons are suitable. Using this technique, matrices in various configurations and shapes suitable for use in vitro and in vivo can be prepared.

It is also contemplated that matrices containing the protein be combinations of one or more hydrogel, sol-gel, and dialysis membranes. For example, a protein entrapped or encapsulated within, a hydrogel or sol gel can be placed within a dialysis membrane of a suitable shape and size as well provide for implantation within a subject, or to manipulate mass-transport properties or permeability to the analytes of the matrix.

The matrix entrapped or encapsulated binding protein sensors of this invention are capable of measuring or detecting micromolar to molar analyte concentrations without reagent consumption. In some embodiments, their sensitivity to analyte may enable the sensors, to be used to measure the low analyte concentrations known to be present in low volume samples of interstitial fluid. The implantable biosensors may, in some embodiments, be implanted into or below the skin of a mammal's epidermal-dermal junction to interact with the interstitial fluid, tissue, or other biological fluids. The protein sensors of the present invention provide for the means to monitor analyte continuously, episodically, or "on-demand" as would be appropriate to the user or to the treatment of a condition.

In other embodiments, sensitivity of the biosensors to analyte (for example glucose) is such that they may be used to test blood analyte levels or the concentration of analyte in a biological solution or other solution may be determined.

In some embodiments, the present invention involves glucose sensors that are capable of measuring micromolar glucose concentrations without reagent consumption. Because of their high sensitivity to glucose, mutant GBP's may be used to measure the low glucose concentrations known to be present in extracted interstitial fluid. Samples from interstitial fluid are known to be painlessly available using methods which perturb the outermost layer of skin, the stratum corneum, for example by laser ablation and weak suction.

A glucose sensor or monitor based on GBP can be expected to display a number of favorable features. The use of a single sensor promises a fast response time, limited by the rate of glucose transport to the protein. For a GBP-based sensor, the only motion needed is of the two domains of the proteins, which should readily occur even in polymeric supports.

The spectral changes of the present invention can be measured with low cost devices. Excitation for nanosecond lifetime-based sensing can be accomplished with laser diodes, light emitting diodes (LEDs), or electroluminescence light sources. Based on these advances in low-cost fluorescence detection, sensors based on the proteins of the present invention may be used in hand-held devices for real time monitoring of analytes, such as glucose.

For example, a sensor of the present invention may be used in a flow injection analysis (FIA) apparatus or a microfluidic device where a tiny amount ($\leq 1$ μl) of the sample is pumped into a mixing chamber containing either a solution of the protein or a label with immobilized protein and a buffer solution. The mixing chamber preferably has an optically clear window. The excitation source and detector are preferably positioned outside this window with no direct contact with the sample.

Arrays

In some embodiments, the present invention is directed to a detector array. The proteins of the array may have high specificity or may have broad specificity (i.e., promiscuous proteins). Application of analyte(s) to the detector array and binding of the analyte(s) to the proteins and/or variants thereof causes a detectable change in the properties of the first detectable quality depending on the nature of the interaction between the analyte(s) and the proteins, measurement of which allows collection of data for identification or "fingerprinting" of the analyte(s). The invention also provides the use of a detector array in the identification of a sample analyte, as well as methods for the formation of the detector array.

In an embodiment of this aspect of the invention, there is provided a detector array comprising a plurality of discrete proteins immobilized onto or within a solid support. Each protein has an analyte-binding site capable of binding a broad range of structurally diverse analytes. The proteins are provided in groups, each group comprising at least one protein. Each protein may comprise first and second detectable qualities.

In some embodiments, the number of distinct types of proteins in the detector array will be that sufficient to enable formation of a reference database such that the database contains sufficient information to allow accurate identification of a test compound. Typically, the detector array will include at least two distinct types of proteins, preferably from 2 to 250 proteins, and most preferably from 25 to 250 proteins.

The arrays of the present invention may be made by techniques known in the art. For example, the arrays of the present invention may be made using techniques similar to those disclosed in U.S. Published Application No. 20020168692 to CASS, which is incorporated by reference herein.

Methods of Using

The proteins and sensors of the present invention may be used in various sensing methods and techniques known to those skilled in the art.

In some embodiments, the present invention is directed to a method for characterizing a sample. The method includes contacting a protein sensing molecule with the sample, wherein the protein sensing molecule is capable of binding an analyte in the sample. The protein sensing molecule comprises a first detectable quality that changes in a concentration dependent manner when the protein sensing molecule is bound to the analyte, and a second detectable quality that does not undergo substantial change when the protein sensing molecule is bound to the analyte. The method also includes measuring the detectable qualities of the protein sensing molecule, and analyzing the detectable qualities to characterize the sample.

In another embodiment, the method involves contacting a protein with the sample, wherein the protein comprises a first detectable quality having a detectable quality that is affected by analyte binding and a second detectable quality having a detectable quality that is substantially unaffected by analyte binding. The method also includes measuring the detectable quality of the first and second detectable qualities. The method further includes analyzing the detectable quality of the first and second detectable qualities to characterize the sample.

In another embodiment, the present invention is directed to a method for determining the presence or concentration of an analyte in a sample. This embodiment includes contacting a protein with the sample, the protein comprising an analyte-binding site, a first detectable quality having a detectable quality that is affected by analyte binding at the analyte-binding site, and a second detectable quality having a detectable quality that is substantially unaffected by analyte binding at the analyte-binding site. This embodiment also includes measuring any change in the detectable quality of the first and second detectable qualities to determine the presence or concentration of analyte in the sample.

In still another embodiment, the present invention is also directed to a method for determining the presence or concentration of an analyte in a sample. This embodiment includes contacting a protein with the sample, the protein comprising an analyte-binding site, a polarity-sensitive label having a detectable quality that is affected by analyte binding at the analyte-binding site, and a long-lived metal complex label having a detectable quality. This embodiment further includes measuring any change in the detectable quality of the polarity-sensitive label and the long-lived metal complex label to determine the presence or concentration of analyte in the sample.

Samples may be in gaseous, liquid, or solid form (or combination thereof such as in the form of solid samples, gaseous samples extracted from the atmosphere, liquid environmental samples (for example from a contaminated site), gaseous biological samples, such as exhaled air or liquid biological samples such as saliva, blood, serum, sweat, urine, milk, bone marrow, cerebrospinal fluid, synovial fluid, amniotic fluid, or lymphatic fluid. Samples may also be volatile. Solid samples may be processed in a suitable solvent, such as water or organic solvents, to produce liquid samples. Solid samples may also by pyrolyzed to produce gaseous samples. The components of samples are preferably of low molecular weight.

The sensitivity of the protein may be affected by a number of controllable factors. Apparent binding constant, protein concentration, and detectable characteristic, e.g., type of fluorophore, are three major factors that affect the protein's responsive ranges.

The sensitivity of the proteins allows characterization of small samples. The sample size may, e.g., range from about 0.1 µl to about 10 ml, about 1 µl to about 1 ml, about 10 µl to about 500 µl, or about 50 µl to about 250 µl. In some embodiments, larger samples are characterized by taking a small sample from the larger sample.

Considering the small size of the samples that may be measured, it may be important to control evaporation from the sample. To correct for the effect of volume change, the volume of the sample may be measured at the beginning and the end of the measurement and/or cell culture. In some embodiments, the change in sample volume may be eliminated or minimized by using techniques known in the art, e.g., by using a water-saturated atmosphere.

The sensitivity of the proteins also allows measurements in media having a low concentration of analyte. The concentration of analyte may range, e.g., from about 0.01 µM to about 1 M, about 0.1 µM to about 750 mM, about 1 µM to about 500 mM, about 10 µM to about 100 mM, or about 100 µM to about 50 mM. For example, a GBP may be used to monitor glucose at concentrations of 0-100 mM.

High concentration samples may be characterized by first diluting the sample. Thus, the sensitivity of the proteins allows for dilution of the sample. Dilution of samples eliminates the effects of background interference, e.g., fluorescence from the culture media.

For example, the high sensitivity of the protein of the present invention permits the dilution of the cell culture media like DMEM by 1000× or more. At this level of dilution the interferences from other fluorescent components in the media are almost completely eliminated. Additionally, compounds that could potentially bind with the protein at high concentrations are unable to compete with the analyte after dilution.

Because of their small sample volume requirements and high sensitivity, the proteins of the present invention have wide applications in high-throughput bioprocessing.

In one embodiment, a GBP of the present invention is used to monitor glucose in LB media. In some embodiments, glucose may be measured in low-glucose media, such as Luria-Bertani (LB) broth used in bacterial fermentations. The control of glucose concentrations in LB fermentations can have an important impact on productivity and purity of products.

In still another embodiment, a GBP is used to measure glucose in interstitial fluid. Interstitial fluid may be extracted through the skin by iontophoresis, i.e., by application of a mild electrical current. The extracted interstitial fluid contains micromolar amounts of glucose that may be correlated to blood glucose levels. Thus, another application where micromolar sensitivity may be useful is in measuring glucose in extracted human interstitial fluid, e.g., extracted by iontophoresis.

In some embodiments such as those involving arrays, further diversity in the specificity and/or affinity characteristics of the protein can be desirable. Increased diversity may result in additional data further characterizing the analyte being analyzed. Such diversity may be achieved by, for example, varying the conditions under which the protein is contacted with the sample. Thus, the temperature, pH, and/or salt concentration may be altered to achieve such diversity.

Generally, the methods of the present invention may be carried out at any temperature that is not deleterious to the sample and protein. According to one preferred embodiment, the sample is examined at ambient temperature. According to an alternate preferred embodiment, the sample is examined at reduced temperature, i.e., a temperature below ambient temperature, such as less than about 20° C., less than about 15° C., less than about 10° C., less than about 5° C., less than about 0° C., less than about −5° C., or less than about −10° C. According to another alternate preferred embodiment, the sample is irradiated at elevated temperature, i.e., a temperature above ambient temperature, such as greater than about 30° C., greater than about 37° C., greater than about 60° C., greater than about 72° C., or greater than about 80° C. Suitable temperature levels can be determined empirically by one skilled in the art.

For the L255C mutant described above, the maximum signal changes and apparent binding constants increased with temperature. The relations between the maximum signal changes, apparent binding constants, and temperature can be used to predict or correct for the effect of temperature on glucose measurements. By changing the operating temperature, the sensor response range may be tuned.

Generally, according to the methods of the present invention, the pH of the sample is about 7. In some embodiments of the present invention, however, the sample may have a pH of less than about 7, such as less than or equal to about 6, less than or equal to about 5, less than or equal to about 4, or less than or equal to about 3. In alternative embodiments of the present invention, the sample may have a pH of greater than about 7, such as greater than or equal to about 8, greater than or equal to about 9, greater than or equal to about 10, or greater than or equal to about 11. Suitable pH levels can be determined empirically by one skilled in the art.

Generally, the methods of the present invention may be carried out at any salt concentration that is not deleterious to the sample and protein. The method may be carried out at a salt concentration of less than about 0.1 mM, less than about 0.01 mM, or less than about 0.001 mM. The method may also be carried out at a salt concentration of greater than about 0.1 mM, greater than about 1 mM, greater than about 10 mM, greater than about 100 mM, or greater than about 1 M. Suitable salt concentrations can be determined empirically by one skilled in the art.

The methods and arrays of the present invention may be used in a variety of different applications, such as identifying particular compounds or groups of compounds in a sample. For example, they may be used to detect pathogens, such as bacteria, fungi, or viruses in environmental or biological samples. They may be used to detect molecules associated with and/or indicative of pathological states. They may also be used to detect chemical contamination in environmental samples such as air or water.

In one embodiment, the present invention provides a method for providing a detector array system. The method includes contacting a detector array as described above with a panel of known test analytes. The method further includes measuring the characteristics of the first and second detectable qualities for each protein upon analyte binding to produce a data array pattern. The data array pattern may be used to generate a reference database of the patterns.

In a related embodiment, the above method for providing a detector array system may be supplemented by contacting the array with a sample containing a sample analyte. This embodiment also includes producing a data array for the sample analyte. The data array of the sample analyte may be compared with the reference database.

In one aspect, the detector array of the present invention may be used to screen for compounds ("candidate analytes") having a desired activity or property. This use of the detector array will have particular advantages in accelerating the screening of new compounds. By utilizing this method of the invention, it is possible to screen a large number of analytes rapidly and obtain a rapid elimination of analytes with no or low probability of exhibiting the desired activity. The analytes which are determined to be of potential interest may then be screened in more complex systems which would be impractical or cumbersome to use on a large scale with a large number of candidate analytes, or which are more difficult or expensive to configure reliably (e.g., receptor binding, cell growth or inhibition assays and the like).

In view of the above, the proteins of the present invention may be used in an array in a manner similar to that disclosed in U.S. Published Application No. 20020168692 to CASS, which is incorporated by reference herein.

Modulation Sensing

In one embodiment, the protein of the present invention is used in modulation sensing. Modulation sensing is described in LAKOWICZ et al., Anal. Chem., 70:5115-5121 (1998), which is incorporated by reference herein. In general, modulation sensing involves lifetime-based sensing techniques, in which fluorophores or sensing schemes are identified that display an analyte-dependent change in the sample's decay time, and the change in decay time is used to determine the concentration of the analyte. The basic idea is to use a nanosecond fluorophore with a long-lived fluorophore. For such a mixture the modulation of the emission at intermediate frequencies becomes equivalent to the fraction of the total emission due to the short lifetime nanosecond fluorophore. This occurs because the emission from the long-lived fluorophore is demodulated and that of the nanosecond fluorophore is near unity.

More specifically, for a mixture of fluorophores, the phase and modulation can be calculated using the sine and cosine transforms of the intensity decays, $N_\omega$ and $D_\omega$, respectively, at a given frequency $\omega$ $$N_\omega = \Sigma f_i m_i \sin \Phi_i, \quad (1)$$

$$D_\omega = \Sigma f_i m_i \cos \Phi_i, \quad (2)$$

where $f_i$ is the fractional steady-state intensity, $\Phi_i$ is the phase, and $m_i$ is the modulation. The modulation at frequency $\omega$ is given by $$m = (N^2 + D^2)^{1/2} \quad (3)$$

For example, in the case of Ru-GlnBP-Acr, the difference in lifetime between Ru and Acr is large. It is therefore reasonable to assume that a frequency ω can be identified where the modulation of Acr is close to 1.0 while the modulation of Ru is close to 0.0. At this frequency, $$N = f_{Acr} \sin \Phi_{Acr}, \quad (4)$$

$$D = f_{Acr} \cos \Phi_{Acr}. \quad (5)$$

Using equation (3) yields:

$$m = f_{Acr} \quad (6)$$

This final conclusion proves that the modulation of a label emitting both short and long-lived components is the fractional intensity of the short-lived component. The implication is that signal transduction need not be accompanied by lifetime changes but can be limited to intensity changes of the short-lived component. Additionally, the modulation changes are observed at frequencies lower than those required if the only emitting species is the short-lived dye. These lower frequencies allow for the design of simpler, low-cost instrumentation.

For example, this method allows sensing based on modulation from about 1 to 10 MHz. In one embodiment, a glutamine-binding protein with acrylodan and a long-lived ruthenium complex allowed for modulation sensing at lower frequencies (1-10 MHz) approaching an accuracy of ±0.02 μM glutamine.

Additionally, the nanosecond sensing fluorophore does not need to display a change in lifetime (τ). A simple change in intensity in response to the analyte is adequate for a low-frequency modulation sensor.

Lifetime-based sensing is most often performed using the phase-modulation method. The use of phase angles (Φ) or decay times can be preferable to intensity-based sensing because decay times are mostly independent of changes in label concentration or total signal level and can be measured in turbid media and even through skin. Because the modulation is independent of total signal level, modulation sensing can be accurate even if there are changes in signal level due to changes in the position of the sample or flexing of fiber optics. What is necessary is that the relative proportions of short and long-lifetime fluorophores remain the same. The calibration curve will change if the relative intensities of the fluorophores change in a manner independent of analyte concentration. For example, if the first and second detectable qualities photobleach at different rates, the modulation sensor calibration curves will change.

Thus, in one embodiment of a modulation sensor, a short-lived label is combined with a long-lived label, such as a metal-ligand complex. At low frequencies, the modulation of the combined emission of analyte sensitive short-lived label and the long-lived metal-analyte complex depends on the fractional fluorescence intensity of the shorter lifetime species. The fractional intensity decreases on binding analyte, resulting in a decrease in the modulation that can be used to measure the analyte concentration.

Frequency-domain intensity decay may be measured with instrumentation described in LAKOWICZ et al., Biophys. Chem., 21:61-78 (1985), which is incorporated by reference herein. This instrumentation may be modified with a data acquisition card from ISS, Inc., Urbana, Ill., as disclosed in FEDDERSON et al., Rev. Sci. Instrum., 60(9):2929-2936 (1989), which is incorporated by reference herein. Excitation may be at 325 nm from a HeCd laser modulated with a Pockels cell. Emission spectra may be recorded on an Aminco SLM AB2 spectrofluorometer using an excitation wavelength of 325 nm. Polarizers may be used to eliminate the effect of Brownian rotation.

In considering the opto-electronics required for modulation based sensing, blue light emitting diodes (LEDs) can be amplitude modulated from 0.1 to 100 MHz, and LEDs with ultraviolet output near 380 nm are available and can be modulated to 100 MHz. Electroluminescent devices can also be modulated at MHz frequencies. Hence, simple inexpensive light sources could be used for a modulation glucose sensor.

A device for modulation-based sensing can be simpler than the usual phase-modulation instruments. For phase angle measurements the detector must be modulated with a fixed phase relationship to the modulated excitation. Modulation measurements can be performed without the phase-locked relationship, simplifying the electronics. Accordingly, the present invention includes a portable battery powered sensor.

The sensitivity of this method allows monitoring glucose in interstitial fluid. Because of the high affinity of GBP for glucose, this device could also be used with diluted blood, as the glucose concentration in whole blood is in the mM range.

Ratiometric Sensing

In another embodiment, the protein of the present invention is used in ratiometric sensing. Although the sensitivity of modulation sensing is high, modulation measurements have the disadvantage of requiring careful shielding from ambient light. This can be remedied by calculating the ratio of the modulation at two frequencies: (1) the frequency where no modulation change is detected in the presence of analyte; and (2) the frequency where the emission is modulated.

Thus, in one embodiment, the protein of the present invention is used in dual-frequency ratiometric sensing. Ratiometric sensing is described in KOSTOV et al., Analyst, 125:1175-1178 (2000); and KOSTOV et al., Anal. Biochem., 297:105-108 (2001), both of which are incorporated by reference herein. Ratiometric dyes are desirable because factors such as the concentration of the dye, the intensity of the light source, the path length, and sample positioning are internally corrected.

In other words, the ratio of modulation at two frequencies is correlated to the analyte concentration. This prevents ambient light from interfering with the measurements in, e.g., a low cost semiconductor based ratiometric device.

The theory of ratiometric sensing is discussed in more detail as follows. Let a fluorescent sample emit two emissions with steady-state intensities $A_1$ and $A_2$ and lifetimes $\tau_1$ and $\tau_2$, respectively, with $\tau_1 = 1000\tau_2$. The ratio $A_1/A_2$ is to be determined.

If the sample is excited by modulated light, the AC amplitude A of the emission will be dependent on the excitation frequency, the lifetimes, and the steady-state intensities by the equation $$A = \sum_{i=1}^{2} A_i (1 + \omega^2 \tau_i^2)^{-1/2}. \quad (7)$$

Suppose that $\omega_1 = 0.1/\tau_1$. Then $$A_{\omega 1} = 0.995 \cdot A_1 + A_2 \approx A_1 + A_2. \quad (8)$$

Thus, at relatively low frequencies the amplitude of the total emission equals the sum of both partial emissions. Now, suppose that $\omega_2 = 100/\tau_1$. Then $$A_{\omega 2} = 0.0099 \cdot A_1 + 0.995 \cdot A_2 \approx A_2. \quad (9)$$

In other words, there are frequencies at which the long-lifetime emission is almost completely demodulated, while the short-lifetime emission still retains significant modulation. When the sample is excited at these frequencies, the AC amplitude of the emission is almost exclusively from the short-lived fluorophore.

Consequently, the intensity ratio of the two emissions (regardless of the degree of overlap between the spectra) can be determined by the equation $$\frac{A_1}{A_2} = \frac{A_{\omega 1}}{A_{\omega 2}} - 1. \tag{10}$$

The fact that the discrimination between the emissions is performed through the use of different modulation frequencies rather than through measuring on different wavelengths allows the use of fluorophores with significant overlap in their emission spectra. The excitation unit is simplest if the excitation wavelengths are the same, but when that is not possible, two different sets of excitation LEDs could be used. Given the low cost of the light sources and the ease of their control, this does not overly complicate the measuring system.

As the discrimination between the sensing and the reference dyes is lifetime-based rather than wavelength-based, it is possible to use a simple long-pass filter for the emission collection. This strongly enhances the signal level and allows the use of less sensitive photodetectors. As a result, the whole system (both excitation and emission units) was entirely semiconductor-based, which allows operation in even strong ambient light without damaging the detector.

Ratiometric sensing in fluorescence intensity measurements helps to eliminate errors caused by variations in excitation intensity, as well as possible changes in the length and absorptivity of the light path.

The present invention will be further illustrated by way of the following Examples. These Examples are non-limiting and do not restrict the scope of the invention.

EXAMPLES

Example 1

Glutamine-Binding Protein

GlnBP Expression and Isolation

A plasmid containing the S179C variant of GlnBP was expressed in E. coli strain HB101. To release the periplasmic GlnBP, cells from 150-ml overnight cultures were first pelleted by spinning for 10 min. at 6000 g and resuspended in 3 ml of deionized water. Chloroform (3 ml) was added to the cells, which were vortexed briefly and incubated for 10 min. at room temperature. Then, 12 ml of 20 mM phosphate buffer, pH 7.5, was added. Samples were vortexed briefly and spun for 20 min. at 6000 g. The supernatant containing the periplasmic proteins was then decanted or pipetted into a clean sterile plastic tube. The amount of S179C GlnBP was estimated to be >80% of the total periplasmic extract after sodium dodecyl sulfate-polyacrylamide gel electrophoresis (SDS-PAGE) and staining with brilliant blue G (Sigma-Aldrich, St. Louis, Mo.). Reaction of the crude extract with 6-acryloyl-2-dimethylamino-naphthalene or acrylodan (Molecular Probes, Eugene, Oreg.) followed by SDS-PAGE revealed close to 100% labeling of the GlnBP with almost no detectable labeling of the other proteins. This was determined by illuminating the unstained gel on a UV box to show the fluorescent band corresponding to the dye-labeled protein. A prestained standard protein ladder allowed for the estimation of the molecular weight. Thus, no further purification of the periplasmic extract was necessary.

Fluorophore Coupling

The lone cysteine in S179C was labeled with acrylodan as described in DATTELBAUM et al., Anal. Biochem., 291:89-95 (2001), which is incorporated by reference herein. The labeled protein was separated from free dye by gel-permeation chromatography on a Sephadex G-25 column eluted with phosphate-buffered saline, pH 7.5. The N-terminal of the acrylodan-labeled GlnBP was selectively labeled with ruthenium bis-(2,2'-bipyridyl)-1,10-phenanthroline-9-isothiocyanate by maintaining the pH at 7.5. Ruthenium bis-(2,2'-bipyridyl)-1,10-phenanthroline-9-isothiocyanate was prepared as previously reported in YOUN et al., Anal. Biochem., 232:24-30 (1995), which is incorporated by reference herein. The dual-labeled protein (Ru-GlnBP-Acr) was collected by elution from a Sephadex G-25 column.

Fluorescence Measurements

Steady-state emission spectra were recorded on a Varian Cary Eclipse spectrofluorimeter (Varin Instruments, Walnut Creek, Calif.). Time-resolved luminescence decays were measured on a frequency domain fluorimeter (ISS-Koala, Champaign, Ill.) with the following modifications. Blue LED LNG992CFBW (Panasonic, Secaucus, N.J.) driven by a current source was used as the excitation source. The modulation voltage was applied through bias T. The standard radiofrequency amplifier for the photomultiplier tubes was replaced with a ZHL-6A 1-circuits, Brooklyn, N.Y.) to enhance the low-frequency performance. The excitation light was filtered by 500-, 550-, and 650 FL07 short-wave pass filters (Andover, Salem, N.H.). The emission light was filtered by a 500 FH90 long-wave pass filter (Andover). Luminescence decay data were analyzed by nonlinear least-squares methods.

Results

Figure 2:
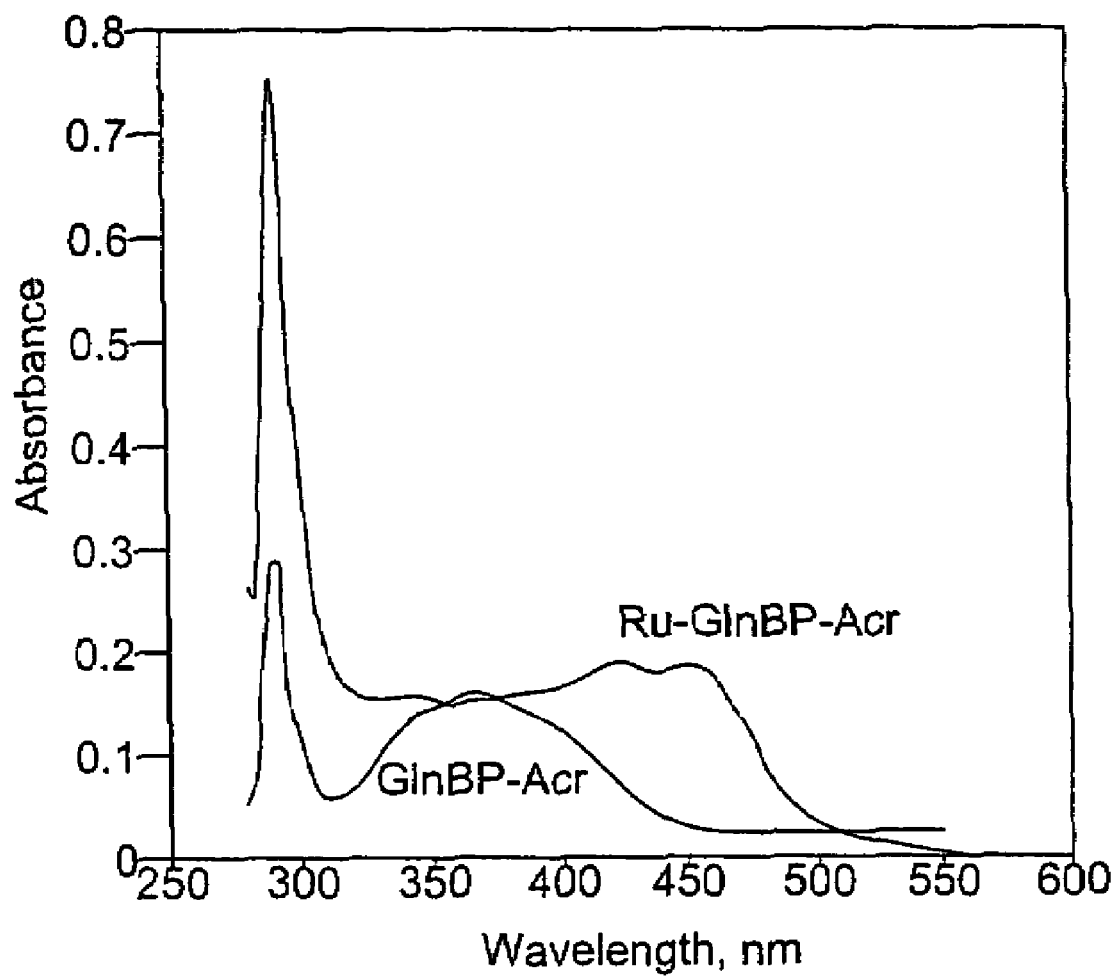
FIG. 2 shows absorbance spectra of acrylodan-labeled glutamine-binding protein (GlnBP-Acr) and glutamine-binding protein labeled with ruthenium and acrylodan (Ru-GlnBP-Acr).

The absorbance spectra of Ru-GlnBP-Acr and GlnBP-Acr are shown in FIG. 2. Total protein concentration for both samples determined by the brilliant blue G-perchloric acid colorimetric assay (Sigma Diagnostics, St Louis, Mo.) was 9.0 µM. The calculated amount of protein-bound acrylodan based on an extinction coefficient of 20,000 cm$^{-1}$M$^{-1}$ was 7.8 and 7.5 µM in GlnBP-Acr and Ru-GlnBP-Acr, respectively, or about 86% labeling efficiency. This was consistent with the estimated >80% GlnBP in the periplasmic extract after SDS-PAGE as described above. The absence of cysteine-containing proteins in the periplasm was an advantage in this case because further purification of the periplasmic fluid was not absolutely necessary. The calculated amount of protein-bound ruthenium based on an extinction coefficient of 15,000 cm$^{-1}$M$^{-1}$ was 12.0 µM.

Figure 3:
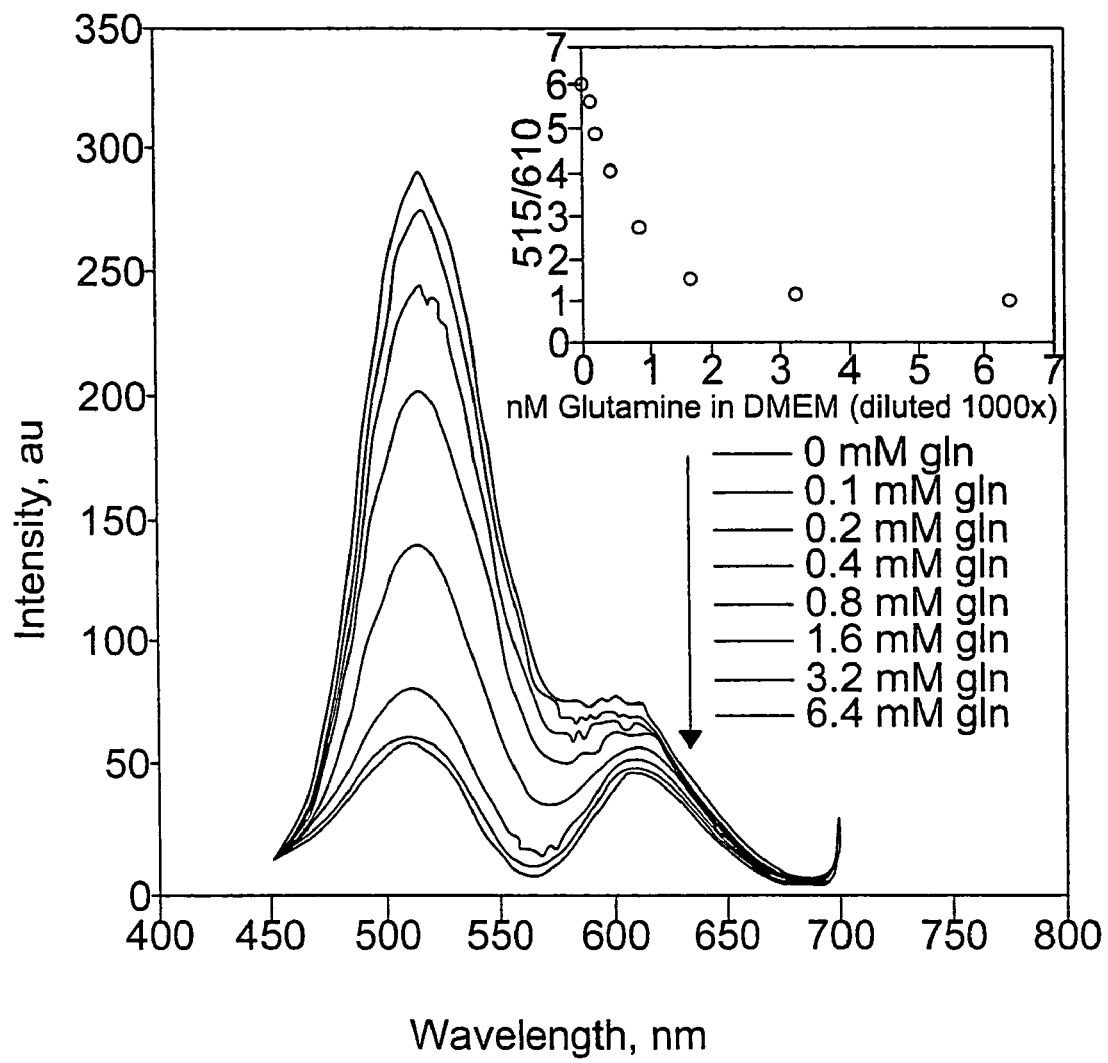
FIG. 3 shows emission spectra of 2.0 µM Ru-GlnBP-Acr in increasing concentrations of glutamine. Glutamine solutions were prepared in Dulbecco's modified Eagle medium (DMEM) and diluted 1000× with phosphate-buffered saline (PBS). The excitation wavelength was 360 nm. The inset of FIG. 3 shows the ratios of emission intensities at 515 and 610 nm plotted as a function of glutamine concentration.

FIG. 3 shows the emission spectra of Ru-GlnBP-Acr in the presence of glutamine. This figure seeks to illustrate two things. First, the fluorescence intensity of acrylodan ($\lambda_{max}$=515 nm) decreased with increasing concentration of glutamine. Concurrently, the luminescence intensity of Ru remained constant at $\lambda_{max}$=610 nm. Second, the standard solutions of glutamine (0.1 to 6.4 mM) were prepared in glutamine-free Dulbecco's modified Eagle media (DMEM), a commonly used media for tissue culture. The resulting solutions were then diluted 1000x with PBS and used in the assay. The submicromolar sensitivity of the protein for glutamine remained virtually unchanged from that observed with the acrylodan label alone, as shown in DATTELBAUM et al., Anal. Biochem., 291:89-95 (2001), which is incorporated by reference herein. This shows that the Ru label in the N-terminal had no effect on the binding activity of the protein.

More importantly, the other components present in the complex DMEM media did not interfere with the binding of glutamine. The inset in FIG. 3 is the ratio of the intensities of acrylodan and Ru ($I_{515}/I_{610}$) as a function of glutamine concentration. The apparent binding constant $K'_d$ for a single binding site was calculated from these data to be 0.72±0.10 μM glutamine. This was close to the reported 100-300 nM dissociation constant for the wild type.

Figure 4:
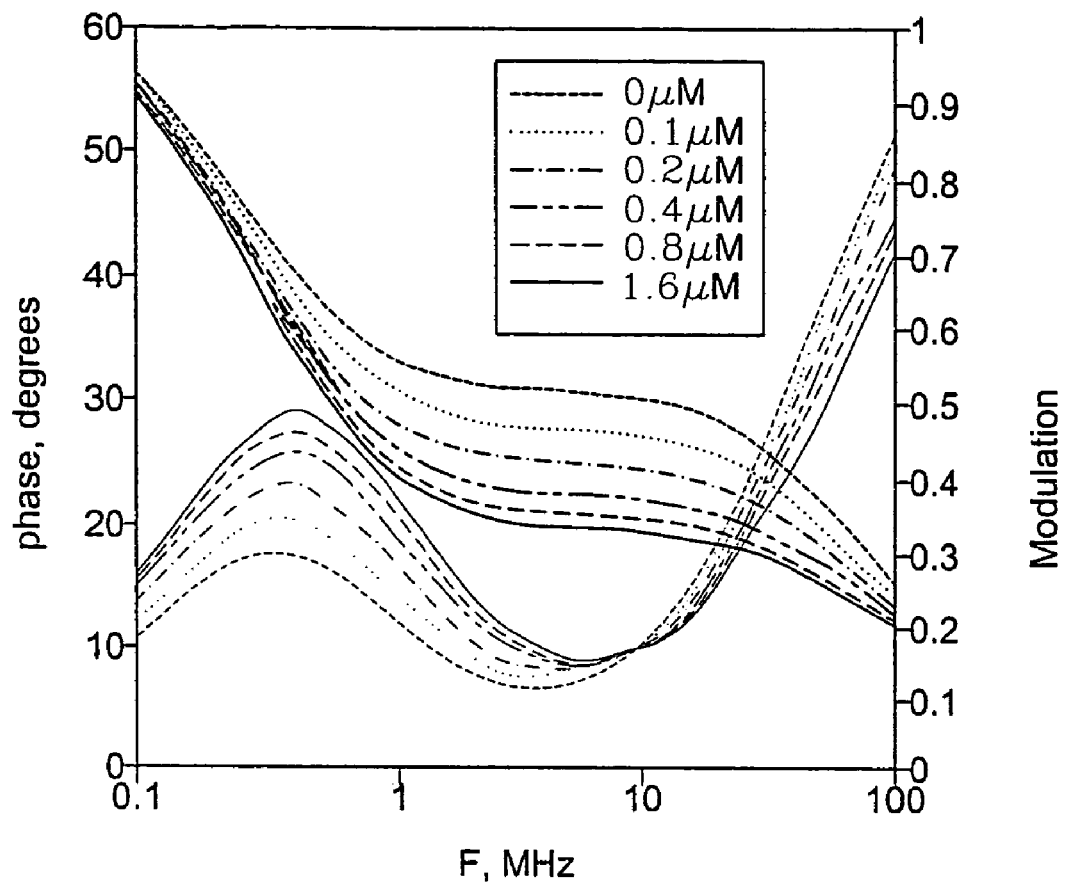
FIG. 4 shows frequency-domain intensity decay traces of 5.0 µM Ru-GlnBP-Acr in 0 to 1.6 µM glutamine.

Frequency-domain intensity decay data are shown in FIG. 4. The data were fit by the least-squares method to a biexponential decay to obtain the approximate lifetimes and fractional intensities of acrylodan and ruthenium as listed in Table 3, below.

TABLE 3

| Glutamine (μM) | $\tau_{Ru}$ (ns) | $f_{Ru}$ | $\tau_{Ru}$ (ns) | $f_{Acr}$ |
|---|---|---|---|---|
| 0.0 | 676 | 0.490 | 2.36 | 0.510 |
| 0.1 | 683 | 0.539 | 2.25 | 0.476 |
| 0.2 | 687 | 0.585 | 2.11 | 0.415 |
| 0.4 | 682 | 0.626 | 1.90 | 0.374 |
| 0.8 | 693 | 0.653 | 1.78 | 0.347 |
| 1.6 | 688 | 0.669 | 1.66 | 0.331 |

As expected, the lifetime of acrylodan decreased from 2.4 to 1.7 ns with the binding of glutamine while the lifetime of Ru remained practically the same at about 685 ns. The ratio of the fractional intensities of acrylodan to Ru decreased from 1:1 to 1:2.

Figure 5:
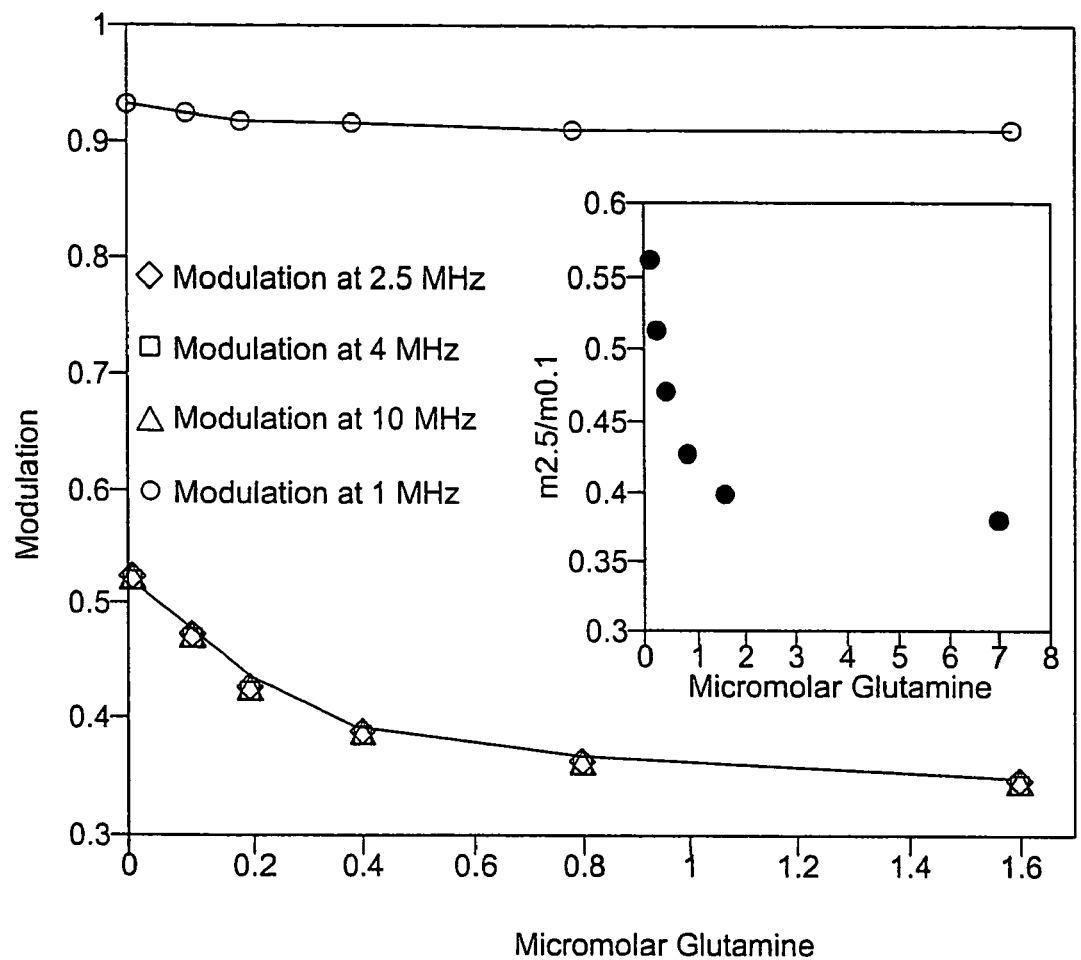
FIG. 5 shows modulation data at 0.1, 2.5, 4, and 10 MHz as a function of glutamine concentrations. The inset of FIG. 5 shows ratios of modulations at 2.5 and 0.1 MHz versus glutamine concentration.

The modulation at frequencies 0.1, 2.5, 4.0, and 10 MHz is plotted as a function of glutamine concentrations in FIG. 5. Modulation measurements are easily accurate to ±0.01, which leads to an accuracy of ±0.02 μM glutamine or approximately 1.4 parts per 10 billion. In the data presented here, 0.1 MHz is practically constant at all glutamine concentrations, while the data at 2.5, 4.0, and 10 MHz are responsive to glutamine levels. The inset in FIG. 5 shows the plot for the modulation ratios.

Example 2

Glucose-Binding Protein

Materials

6-Acryloyl-2-dimethylaminonaphthalene (acrylodan) and tris(2-carboxyethyl)phosphine (TCEP) were purchased from Molecular Probes (Eugene, Oreg.). Fucose, sucrose, glucose, DEAE Sephadex A-50, N,N-dimethylformamide (DMF), NaCl, $KH_2PO_4$, $Na_2HPO_4$, $NaH_2PO_4$, and $MgCl_2$ were purchased from Sigma-Aldrich. Tryptone and yeast extract were obtained from Becton Dickinson (Sparks, Md.). All chemicals were used without further purification. Slide-A-lyzer dialysis cassettes were purchased from Pierce (Rockford, Ill.). SStI, PstI restriction enzymes were purchased from Invitrogen Life Technologies. The Quick-Change mutagenesis kit was obtained from Stratagene (Cedar Creek, Tex.).

Construction of the Plasmid

The plasmid JL01 encoding for the wild-type GBP was used as the template for the construction of the L255C GBP mutant. The single-cysteine mutation at position 255 was accomplished using the Quick-Change mutagenesis kit from Stratagene. The 5' primer used for the mutagenesis was GCACTGGCGGGCACCGTATGCAACGATGC TAACAACC (SEQ ID NO. 1). The 3' primer was GGTTGTTAG-CATCGTTGCATA CGGTGCCCGCCAGTGC (SEQ ID NO. 2). Both primers had the desired mutation (underlined). After the PCR, the product was treated with DpnI restriction enzyme to digest the parental supercoiled dsDNA. The mutated plasmid was then transformed into XL-1 Blue supercomponent cells and spread on LB plates with ampicillin. Colonies appeared in 16 h. Four colonies on each plate were selected for making 5-mL overnight cultures, and the plasmids were then extracted using QIAprep Spin Miniprep Kit from Qiagen. The DNA gel (not shown) confirmed the existence of the desired restriction sites: SstI and PstI. All colonies, except one have the insert of correct length. The DNA sequencing data (now shown) verified the presence of the desired mutation (Biopolymer Core Facility, University of Maryland, Baltimore, Md.).

Protein Expression and Purification

The procedure for the expression, release, and purification of the L255C mutant is similar to that described in TOLOSA et al., Anal. Biochem., 267:114-120 (1999), which is incorporated by reference herein. First, 20 mL of LB medium in a 50-mL tube was inoculated with a single colony on the plate and incubated at 37° C. with shaking at 260 rpm for 8-10 h. The seed culture obtained above was then used to inoculate 500 mL of LB medium supplemented with 1 mM fucose in a 1000-mL shake flask. The culture was then incubated at 37° C. with shaking at 260 rpm for 8 h.

To release the periplasmic proteins, the cells in the above culture were first harvested by spinning for 5 min at 13000 g and then washed twice with 40 mL of 10 mM Tris-HCl, 30 nM NaCl, pH 7.5. The cells were collected by centrifugation at 13000 g for 5 min and resuspended in 40 mL of 33 mM Tris-HCl, pH 7.5. After mixing with 40 mL of 40% sucrose, 0.1 mM EDTA, 33 mM tris-HCl, pH 7.5, the suspension is then left at room temperature for 10 min with very slow shaking, followed by centrifugation at 13000 g for 5 min. The periplasmic proteins were released by adding 10 mL of ice-cold 0.5 mM $MgCl_2$ and shaking vigorously in an ice bath for 10 min. Finally, the suspension was centrifuged at 13000 g for 10 min. The total concentration of the periplasmic proteins was determined using Micro Protein Determination (Sigma Diagnostics, Inc., Louis, Mo.). A 10-fold excess of TCEP was added to the protein solutions to prevent the oxidation of the thiol groups. The GBP content in the supernatant was estimated by SDS-PAGE to be ~50%. The crude protein products were then purified on a DEAE Sephadex A-50 column.

Fluorophore Coupling

The L255C GBP mutant has a single-cysteine mutation at position 255, which allows for the specific labeling of an environmentally sensitive, thiol-reactive fluorophore. To label the protein with such a fluorophore, acrylodan, a 10-fold excess of this dye in DMF was added dropwise to the protein solution, and the conjugation was allowed to occur for 4 h at room temperature. The removal of unreacted dye was performed by dialyzing overnight in Slide-A-lyzer dialysis cassettes. For labeling of the second fluorophore, a 10-fold excess of ruthenium bis(2,2'-bipyridyl)-1,10-phenanthroline-9-isothiocyanate in DMF was added to the single-labeled protein solution and the mixture was then allowed to sit for 4 h at room temperature. The N-terminal of the protein was selectively labeled by maintaining the pH at 7.5. The unreacted dye was removed by applying the protein solution to a DEAE Sephadex A-50 column. The protein-dye conjugate was then eluted from the column using increasing amounts of NaCl (0-0.2 M) in phosphate buffer. The fractions were analyzed by SDS-PAGE, and the fractions containing the desired protein were collected. The total protein concentration was determined, and the labeling efficiency was estimated from the total protein concentration and the concentration of protein-bound fluorophore, which was calculated from its absorbance and extinction coefficient. The final product was 0.2 μm filter-sterilized and stored at 4° C.

Fluorescence Measurements

Steady-state fluorescence spectra were recorded on a Varian Cary Eclipse fluorescence spectrophotometer (Varian Instruments, Walnut Creed, Calif.). Absorbance spectra were recorded on a Hewlett-Packard 8432A diode array spectrophotometer. Frequency-domain intensity decays were measured on an ISS-Koala fluorometer (Champaign, Ill.) with several modifications. An ultraviolet LED NSHU550E (Nichia America Corp., Lancaster, Pa.) with a peak wavelength at 375 nm driven by a current source was used as the excitation source. The modulation voltage was applied through bias T.24. The standard radio frequency amplifier for the photomultiplier tubes was replaced with a ZHL-6A (Mini-circuits, Brooklyn, N.Y.) to enhance the low-frequency performance. The excitation light was filtered by 400, 450, 550, and 650 FL07 short-wave pass filters (Andover Corp., Salem, N.H.). The emission light was filtered by a 450FH90 long-wave pass filter (Andover Corp.). All samples were measured in quartz cuvettes (Starna Cells, Inc., Atascadero, Calif.).

Results

Although the mutated plasmid was first transformed into XL-1 Blue supercompetent cells after the mutation was accomplished, this host did not express the new mutant protein very efficiently. To find the best host for protein expression, the mutated plasmid was transformed into several other E. coli strains including NM303, HB101, and JM109. All these cell lines expressed the mutant with comparable efficiency. However, NM303 does not produce the wild-type GBP. Thus, NM303 was chosen as the host for the expression of the L255C mutant. Additionally, unlike the Q26C mutant, the addition of fucose proved to be important for the expression of L255C. Without the addition of 1 mM fucose, the L255C mutant was not efficiently expressed.

Figure 6:
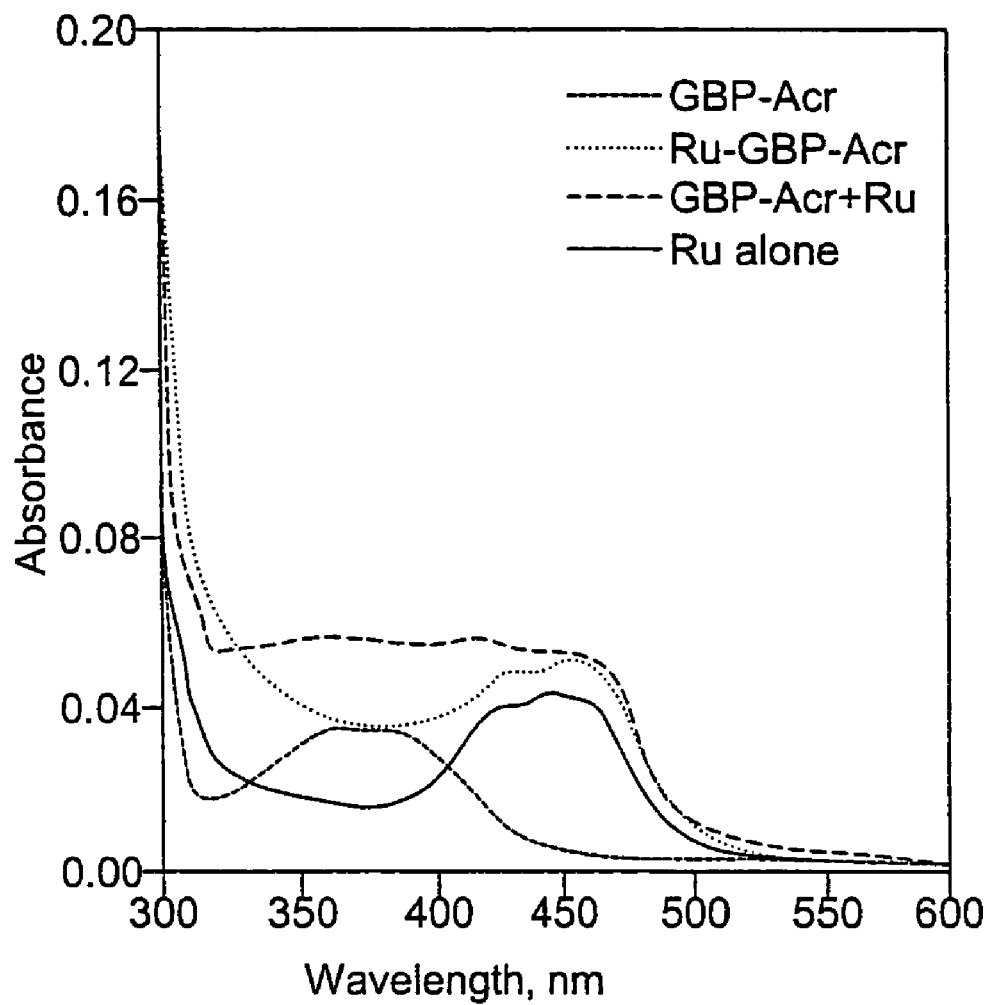
FIG. 6 shows an absorbance spectra of GBP-Acr, Ru-GBP-Acr, ruthenium alone, and GBP-Acr+ruthenium. The total protein concentration was 3.2 µM; the labeling extents of acrylodan and ruthenium were 72 and 94%, respectively.

The absorbance spectra of GBP-Acr, Ru-GBP, Acr, Ru alone, and GBP-Acr+Ru are shown in FIG. 6. The total protein concentration in all samples was 3.2 μM. The calculated labeling extend of protein-bound acrylodan based on an extinction coefficient of 20,000 $cm^{-1}M^{-1}$ was ~72%. The calculated labeling extent of ruthenium based on an extinction coefficient of 15,000 $cm^{-1}M^{-1}$ was 94%.

Figure 7:
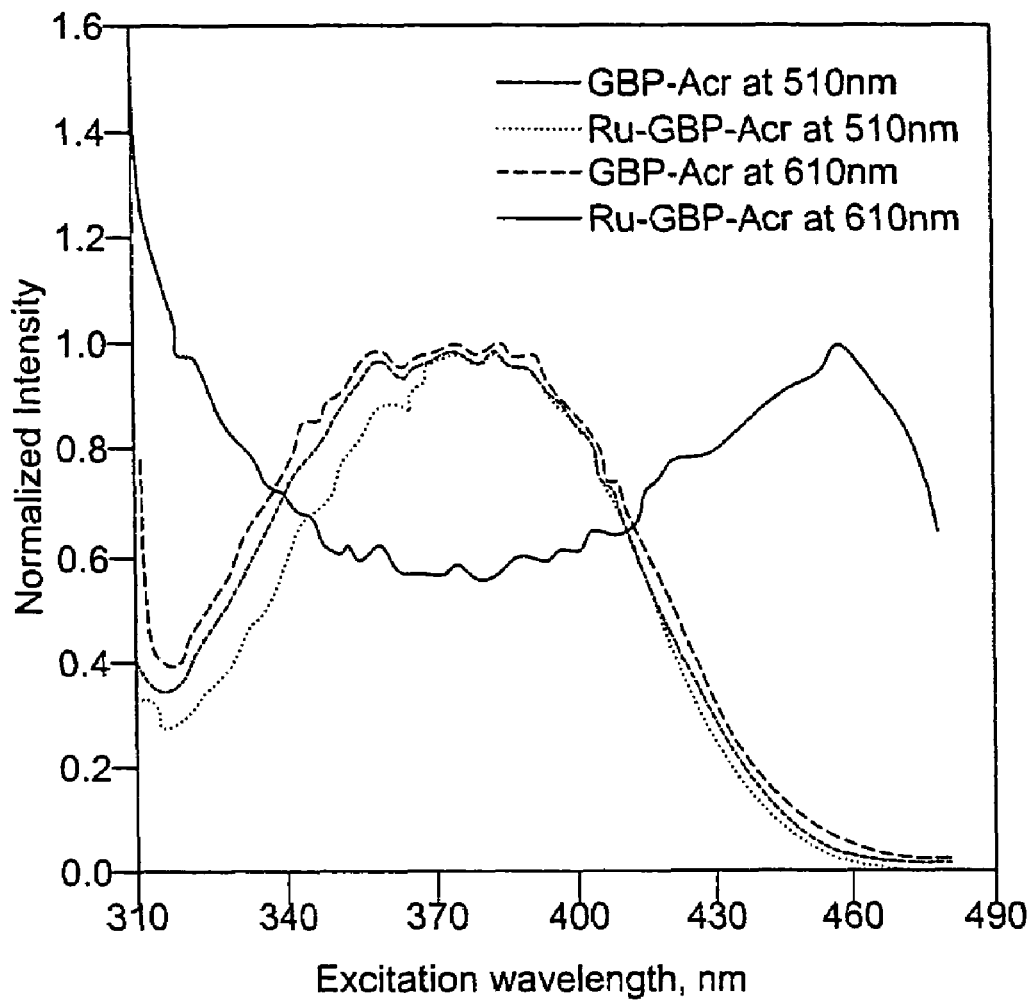
FIG. 7 shows an excitation spectra of GBP-Acr and Ru-GBP-Acr at emission wavelengths of 510 and 610 nm.

FIG. 7 shows the excitation spectra of GBP-Acr and Ru-GBP-Acr, respectively. It can be seen that the excitation spectra monitored at the 510-nm emission exhibits a peak at ~380 nm in both single- and dual-labeled GBP. However, the excitation spectra monitored at 610 nm clearly show a peak at ~460 nm in the dual-labeled GBP, an indication of the presence of ruthenium.

Figure 8A:
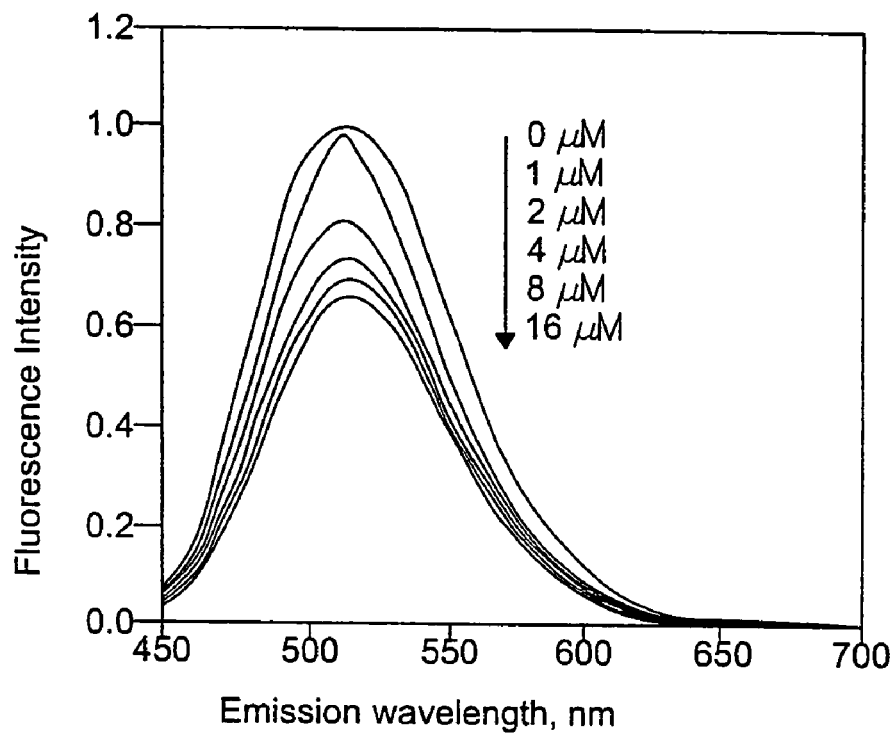
FIG. 8 shows an emission spectra of (FIG. 8a) GBP-Acr excited at 380=m and (FIG. 8b) Ru-GBP-Acr excited at 410 nm in 0-16 µM glucose with maximum fluorescence intensity in 0 µM glucose normalized to unity (solid lines). For comparison, the emission spectra in 16 µM glucose with its maximum intensity normalized to unity are also shown (dotted lines), which indicates that the maximum emission wavelength was slightly red-shifted from 510 to 517 nm upon glucose binding.

The emission spectra of GBP-Acr and Ru-GBP-Acr in the presence of glucose are shown in FIGS. 9a and 9b, respectively. To obtain a larger signal, an excitation wavelength of 380 nm was used for the single-labeled GBP (GBP-Acr). However, for the dual-labeled GBP (Ru-GBP-Acr), an excitation wavelength close to 10 nm should be used in order to obtain comparable fluorescence intensities for acrylodan and ruthenium (FIG. 7). Otherwise, the fluorescence intensity of the ruthenium label will be too low to be used as a reference. FIG. 8 shows that, for both single-labeled and dual-labeled GBP, the fluorescence intensity of acrylodan ($\lambda_{max}$=510 nm) decreased with increasing concentration of glucose. FIG. 8 also shows that the maximum emission wavelength of acrylodan underwent a slight red shift of ~7 nm upon glucose binding. These observations are consistent with the exposure of the fluorophore to the aqueous environment as the protein undergoes conformational changes in the presence of glucose.

Figure 8B:
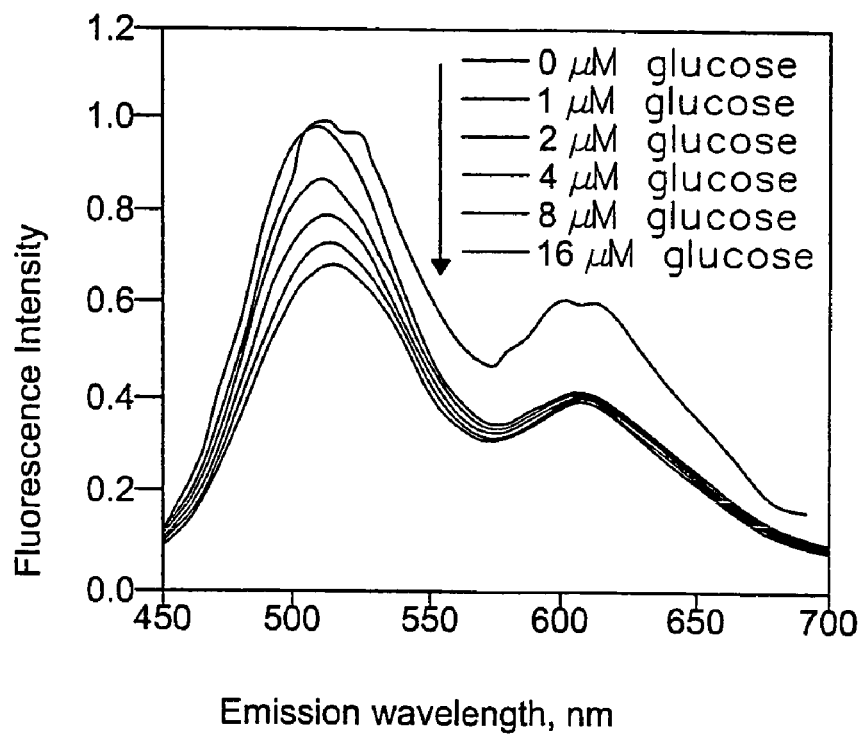

In FIG. 8b, the fluorescence intensity of acrylodan at 510 nm decreases with glucose while the luminescence intensity of Ru at 610 nm remains constant. Thus, the luminescence intensity of Ru can be used as a reference for ratiometric measurements. These measurements were expected to be more impervious to errors due to sample positioning, dye photobleaching, and fluctuations in the excitation light source.

Figure 9:
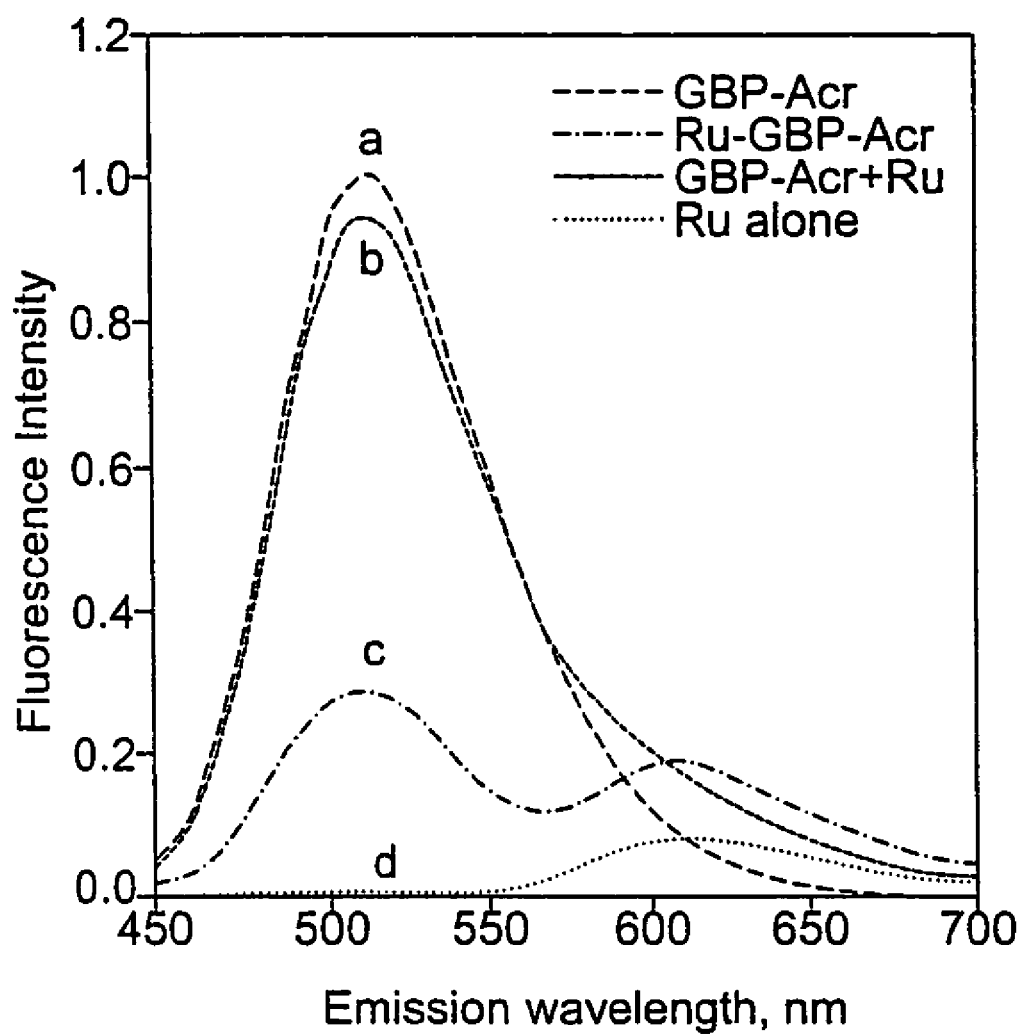
FIG. 9 shows an emission spectra of (a) GBP-Acr, (b) GBP-Acr+ruthenium, (c) Ru-GBP-Acr, and (d) ruthenium alone at an excitation wavelength of 420 nm. No glucose was added.

Examination of the absorbance and fluorescence spectra of acrylodan and ruthenium indicates that FRET between these two fluorophores is possible. When acrylodan and ruthenium are covalently labeled to the same protein, FRET may occur as the acrylodan (donor) and ruthenium (acceptor) are in proximity. This can be observed as a decrease in fluorescence intensity acrylodan in the dual-labeled protein. Indeed, in FIG. 9, the fluorescence intensity of the acrylodan (FIG. 9a) had a 3-fold decrease in emission intensity when ruthenium was labeled to the N-terminal of the same protein (FIG. 9c). Comparatively, the fluorescence intensity of the acrylodan label decreased only slightly when the same amount of free ruthenium was added (FIG. 9b). On the other hand, the ruthenium intensity in FIG. 9b was less than the ruthenium intensity in the dual-labeled (FIG. 9c). All these observations indicate that the decrease in the acrylodan emission from the dual-labeled protein was not caused by inner-filter effects by FRET. Note that FRET between the two fluorophores makes ratiometric measurements possible. As shown in FIG. 9b, the fluorescence intensity of ruthenium was too weak to be used as a reference if no FRET occurs.

Using the equations described in LAKOWICZ, *Principles of Fluorescene Spectroscopy*, 2nd ed.; Kluwer Academic/Plenum Publishers (1999), which is incorporated by reference herein, the Förster distance between the two fluorophores, $R_0$, was estimated to be 29 Å The energy-transfer efficiency between the two fluorophores, E, was estimated to be 70% according to FIG. 9. With both $R_0$ and E being known, the distance between the two fluorophores, r, was then calculated using the following equation:

$$E=R_0^6/(R_0^6+r^6) \tag{11}$$

Figure 10:
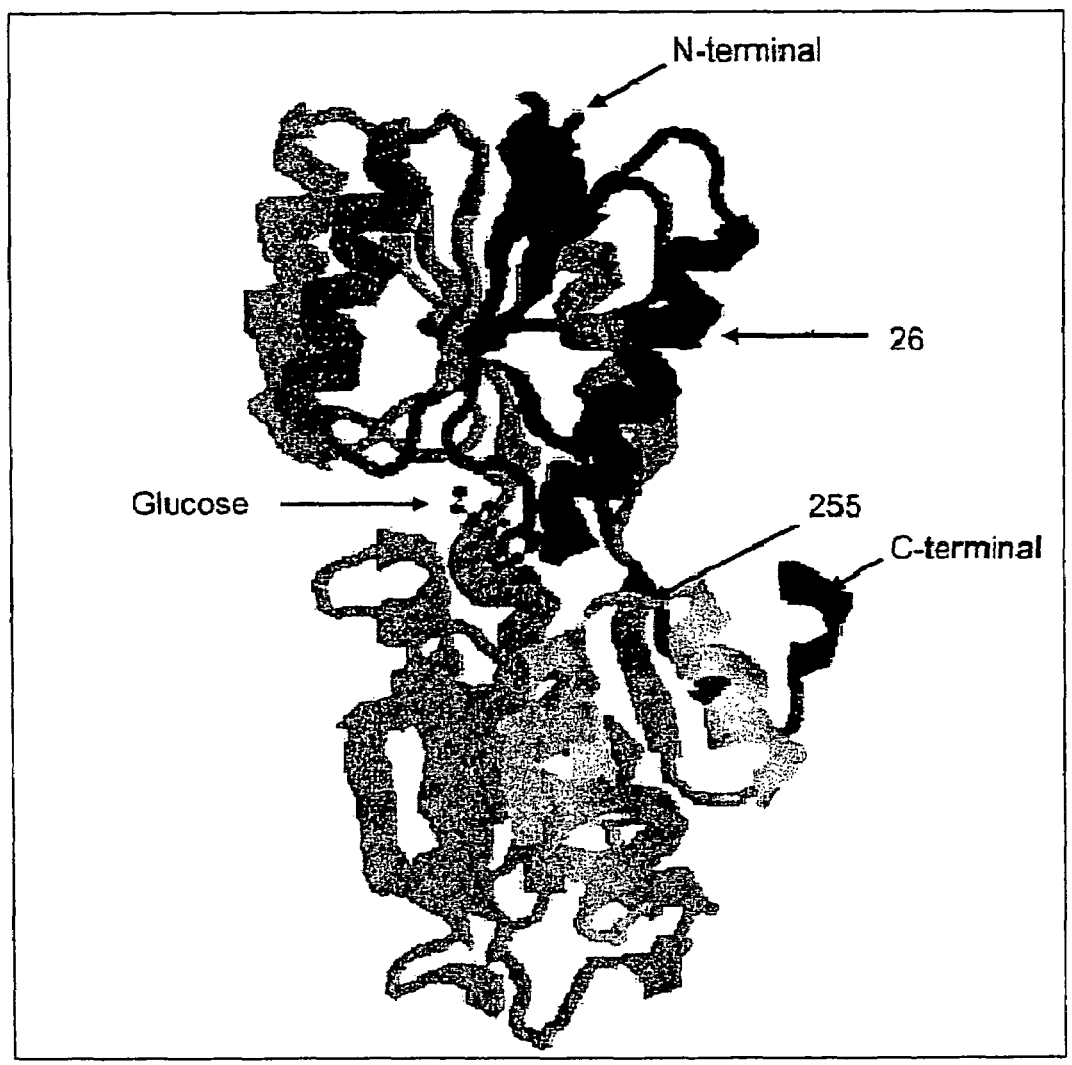
FIG. 10 shows the tertiary structure of GBP Leucine 255 that was mutated to cysteine and labeled with acrylodan.

The result is 25 Å. Since the distance between the two fluorophores is about half the diameter of GBP (FIG. 10), the size of GBP can then be estimated to be ~50 Å. This value was in agreement with that reported from X-ray crystallographic data in MOWBRAY et al., J. Biol. Chem., 258(13):7991-7997 (1983), which is incorporated by reference herein.

Figure 11:
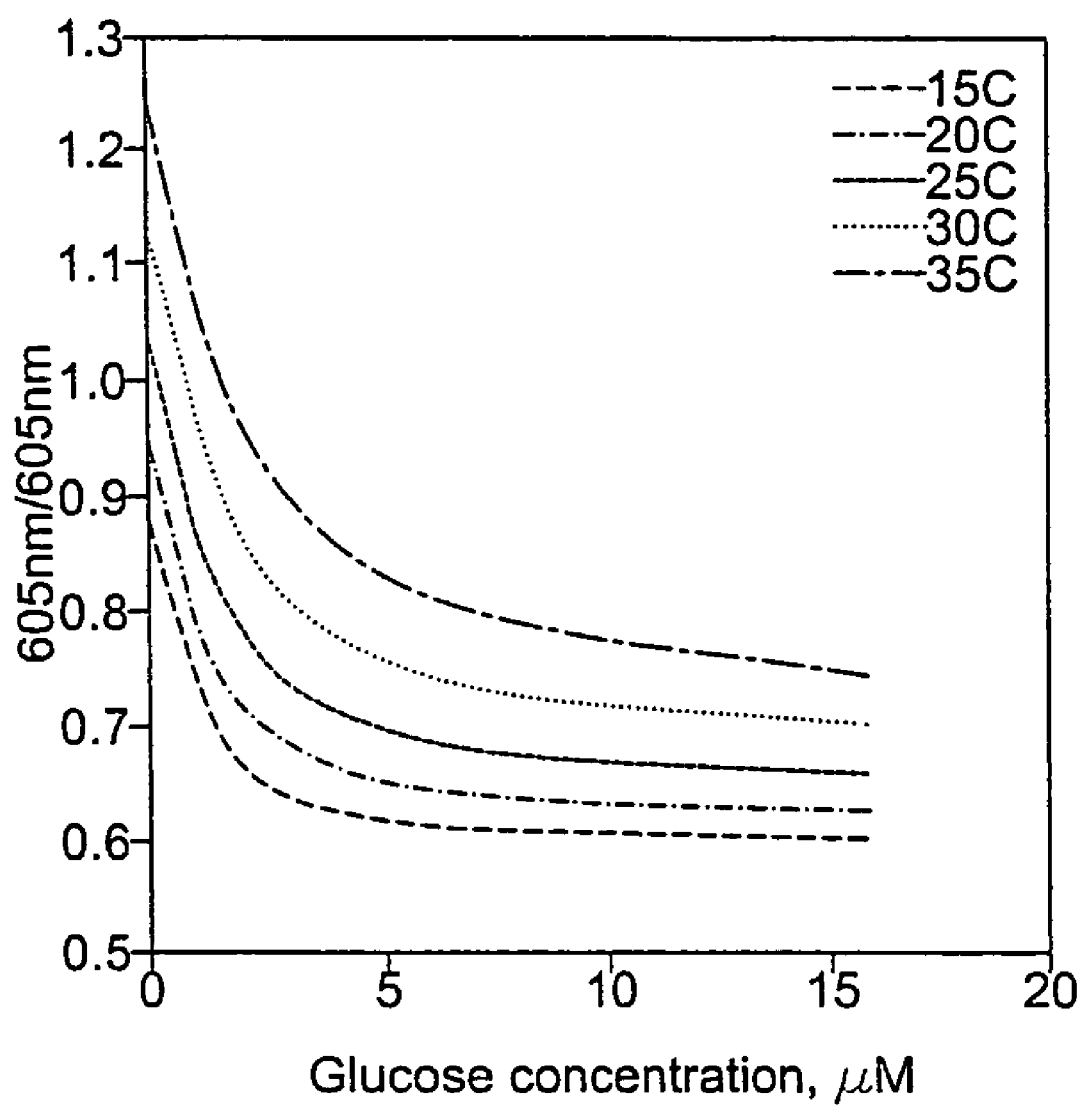
FIG. 11 shows the effect of temperature on the calibration curves of Ru-GBP-Acr. The shown error bars are the standard errors of three repeated experiments.

The effect of temperature on the ratios of the fluorescence intensities of the labeled fluorophores is shown in FIG. 11. It can be seen that the fluorescence intensity ratios increased with temperature. This temperature effect can be attributed to many factors including changes in the equilibrium of analyte binding and the quantum yields of both fluorophores. Temperature also affects dynamic quenching of the fluorophore by the polar solvent. Taken together, theses factors affect the response of the glucose sensor.

Figure 12:
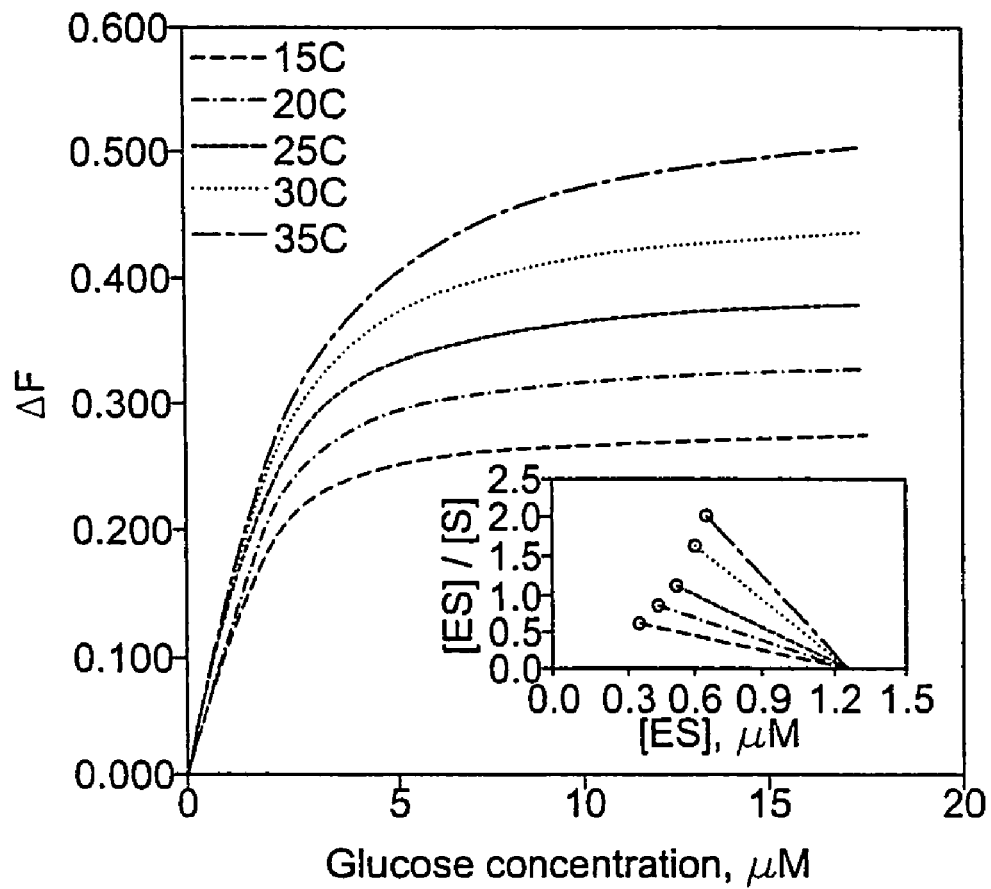
FIG. 12 shows nonlinear fit of experimental results to the binding isotherm. The inset of FIG. 12 is a Scatchard plot of [ES]/[S] versus [ES]. As in FIG. 11, the shown error bars are the standard errors of three repeated experiments.

The apparent binding constants could be calculated by fitting the experimental results to the binding isotherm:

$$\Delta F=\Delta F_{max}[S]/(K_d+[S]) \tag{12}$$

where $\Delta F$ is the normalized signal change at any analyte concentration, $\Delta F_{max}$ is the normalized signal change at saturating analyte concentration, $K_d$ is the apparent binding constant, and [S] is the concentration of the analyte in free state. Together with the equations for single binding equilibria and for mass balance, the following equation can be derived:

$$\frac{\Delta F_{max}}{\Delta F} = 1 + K_d \bigg/ \left( [S]_t - \frac{\Delta F}{\Delta F_{max}} [E]_t \right) \quad (13)$$

where $[E]_t$ and $[S]_t$ represent the total concentrations of GBP and glucose, respectively. The experimental results were analyzed with nonlinear regression and the best results for $\Delta F_{max}$ and $K_d$ are listed in Table 4. In other words, Table 4 shows the best nonlinear fit results of maximum signal changes ($\Delta F_{max}$) and apparent binding constants ($K_d$) at different temperatures. It can be seen that both the maximum signal changes and the apparent binding constants increased with temperature. FIG. 12 gives the comparison between the experimental data and the fitted values. The Scatchard plot of [ES]/[S] (ratio of bound glucose concentration to free glucose concentration) versus [ES] is also shown in the inset. This figure shows that the experimental data conform to equations for a single binding site. The binding constant for the single-labeled GBP at 25° C. was estimated with nonlinear regression. A value of 0.84±0.04 μM was obtained, which is close to that of the dual-labeled GBP, 0.71±0.04 μM. The similarity between the two binding constants shows that the Ru label at the N-terminal has a minor effect on the binding activity of the protein.

TABLE 4

| Temp., ° C. | $\Delta F_{max}$ | $K_d$, μM | $R^2$ |
|---|---|---|---|
| 15 | 0.278 ± 0.001 | 0.42 ± 0.04 | 0.9974 |
| 20 | 0.335 ± 0.001 | 0.55 ± 0.04 | 0.9982 |
| 25 | 0.393 ± 0.001 | 0.71 ± 0.03 | 0.9992 |
| 30 | 0.458 ± 0.001 | 0.91 ± 0.02 | 0.9998 |
| 35 | 0.545 ± 0.003 | 1.42 ± 0.07 | 0.9991 |

The effect of temperature on equilibrium constant is given by $$\frac{d \ln K_d}{dT} = \frac{\Delta H^0}{RT^2} \quad (14)$$

where T is absolute temperature. $\Delta H^0$ is the enthalpy change of the process. R is the gas constant. Suppose that $\Delta H^0$ does not change with the temperature; integration of equation (14) gives $$-\ln K_d = \frac{\Delta H^0}{R} \frac{1}{T} + C \quad (15)$$

where C is a constant.

Using equation (15), the values of $\Delta H^0$ were estimated to be 43.1 kJ/mol. As expected, the dissociation process is endothermic, while the opposite process is exothermic. Thus, for any given temperature the apparent binding constant for this sensor can be estimated as follows:

$$K_d = \exp(17.1 - 5180/T), \mu M \quad (16)$$

Additionally, the maximum signal change and temperature were correlated using a linear equation. The result was $$\Delta F_{max} = 0.01314T - 3.516 \quad (17)$$

Figure 13:
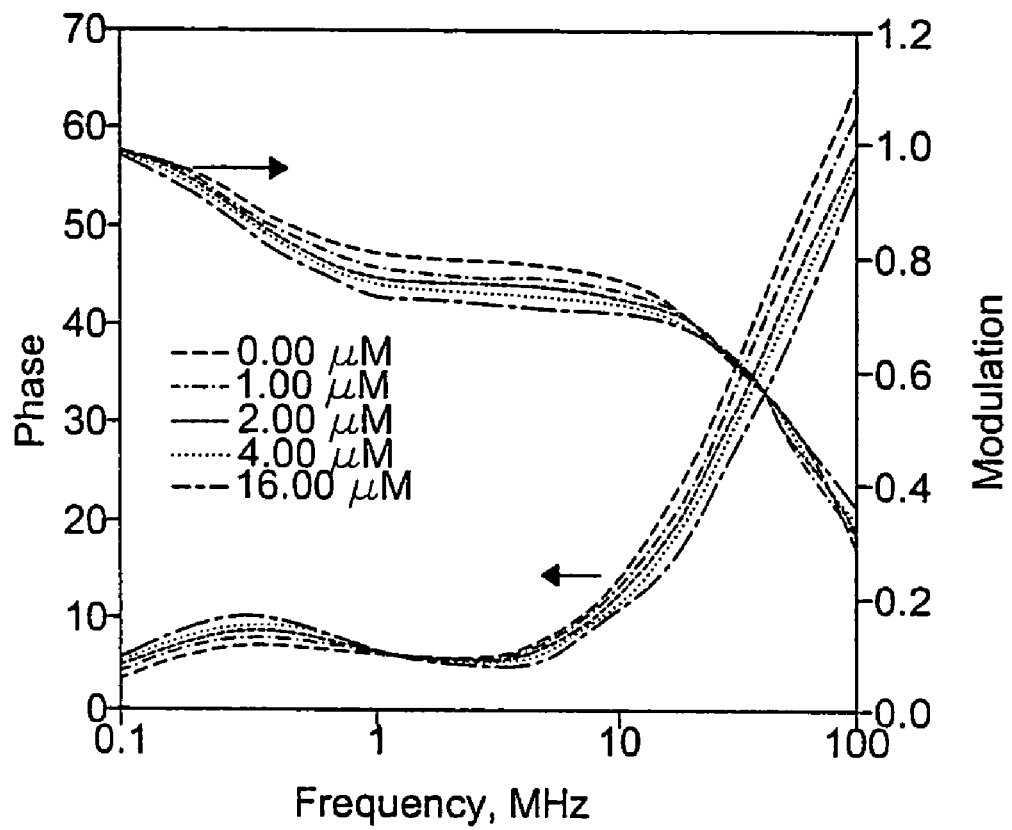
FIG. 13 shows frequency-domain intensity decay traces of Ru-GBP-Acr in increasing glucose concentrations at room temperature.
Figure 14:
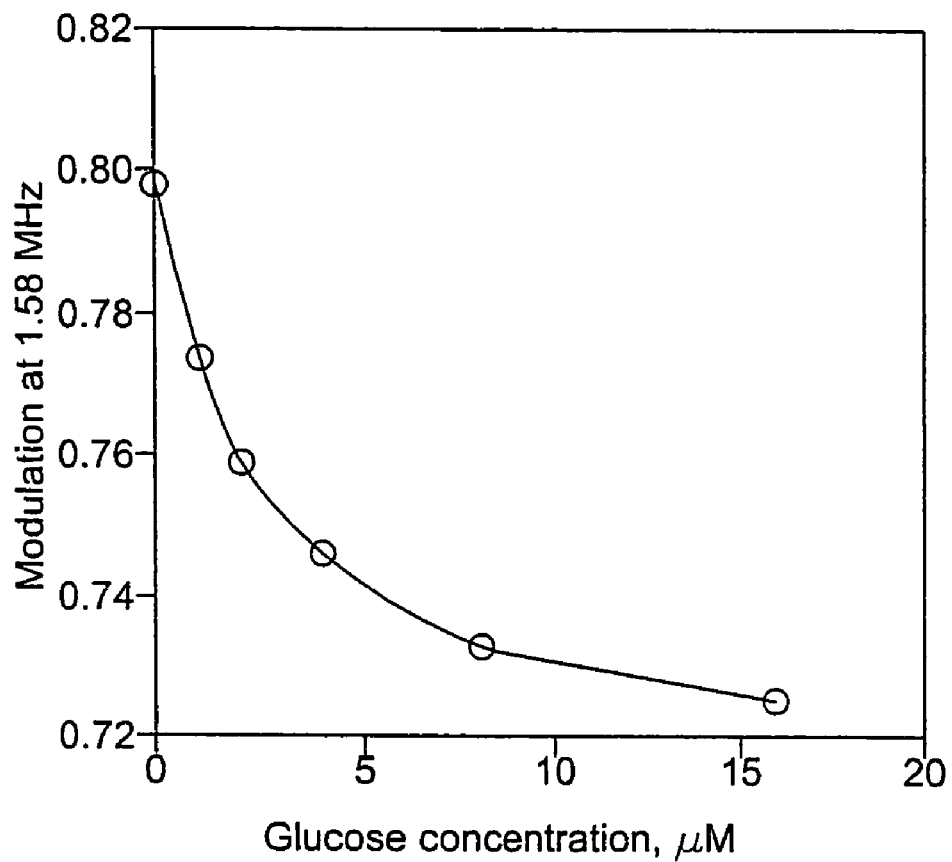
FIG. 14 shows modulation at 1.58 MHz versus glucose concentration.

Beyond ratiometric measurements, the presence of the long-lived ruthenium metal analyte complex in the acrylodan-labeled GBP also allowed for modulation-based sensing at relatively low frequencies. In the absence of ruthenium, changes in the fluorescence lifetime of acrylodan in response to glucose were detected using a fast and expensive laser excitation source at frequencies close to 1 GHz. With ruthenium, the modulation changes were detected between 1 and 10 MHz as shown in FIG. 13. Indeed, the frequency decay traces shown here were collected using a low-cost blue light-emitting diode as excitation source. FIG. 14 shows the modulation at 1.58 MHz as a function of glucose concentration. Knowing that modulation measurements can be accurate to ±0.01, glucose concentration can be conservatively measured to an accuracy of ±0.5 μM from the modulation data.

Examples 3 and 4

Example 3 involves a glucose-binding protein and Example 4 involves a glutamine-binding protein. These Examples illustrate the signal transduction properties and potential applications of these proteins.

Materials 2-(4'-iodoacetamidoanlino)naphthalene-6-sulfonic acid (ANS) and 6-acryloyl(di-menthylamino)naphthalene (acrylodan), tris(2-carbonxyethyl)phosphine (TCEP) were purchased from Molecular Probes (Eugene, Oreg.). Glucose, mannose, galactose, sucrose, fructose, maltose, glutamine, Sephadex G-25, DEAE Sephadex A-50, N,N-dimethylformamide (DMF), chloroform, NaCl, $K_2HPO_4$, $KH_2PO_4$, $Na_2HPO_4$, $NaH_2PO_4$, $MgSO_4$ were purchased from Sigma-Aldrich. Tryptone and yeast extract were obtained from Becton Dickinson (Sparks, Md.). Soy peptone was obtained from DIFCO Laboratories Detroit, Mich.). All chemicals were used without further purification. Dialysis membrane tubing was obtained from Spectrum Medical Industries, Inc. (Los Angeles, Calif.). Slide-A-lyzer® dialysis cassettes were purchased from PIERCE (Rockford, Ill.).

Protein Expression, Purification, and Fluorophore Coupling

The plasmids encoding the mutants were constructed by site-directed mutagenesis as described previously (DATTEL-BAUM et al., Anal. Biochem., 291:89-95 (2001); and TOLOSA et al., Anal. Biochem., 267:114-120 (1999), both of which are incorporated by reference herein). Two different host E. coli cells, NM303 and HB101, were used for the production of GBP. NM303 does not produce the wild type of GBP, but has a low productivity for mutant GBP. Although HB101 produces the wild type of GBP, its presence does not interfere with the labeling of the dye because it does not contain reactive cysteine residues. Transformation and expression of S179C GlnBP was carried out in E. coli strain HB101.

Glutamine-binding protein was released by using the chloroform shock method (DATTELBAUM et al., Anal. Biochem., 291:89-95 (2001), which is incorporated by reference herein). The amount of S179C GlnBP was estimated by using sodium dodecyl sulfate-polyacrylamide gel electrophoresis, which showed that the content of GlnBP in the periplasmic extract was more than 80%. GBP was released by using the osmotic shock method (DATTELBAUM et al., Anal. Biochem., 291:89-95 (2001), which is incorporated by reference herein). The GBP content in the supernatant was about 50%. The total concentration of the binding proteins was determined using Micro Protein Determination (Sigma Diagnostics, Inc., St. Louis, Mo.). A slight excess of TCEP was added into the protein solutions to prevent the oxidation of the thiol groups.

The S179C GlnBP was labeled with acrylodan and separated from the unreacted dye by gel-permeation chromatography (DATTELBAUM et al., Anal. Biochem., 291:89-95 (2001), which is incorporated by reference herein). The labeling of Q26C GBP with ANS was conducted in a similar manner except that an additional purification step was needed because unreacted ANS tends to adsorb on the protein, which cannot be completely removed with Sephadex G-25. The adsorbed free dye gives a higher baseline signal and decreases the relative signal change. To remove the remaining free dye and further purify the protein, the protein solution was applied to a DEAE Sephadex A-50 column (BOOS et al., J. Biol. Chem., 246(3):621-628 (1971), which is incorporated by reference herein). The total protein concentration was determined and the labeling efficiency was estimated from the total protein concentration and the concentration of protein-bound fluorophore, which was calculated from its absorbance and extinction coefficient (HAUGHLAND, *Handbook of Fluorescent Probes and Research Chemicals*, Molecular Probes, Inc. (1996), which is incorporated by reference herein). The final product was 0.2 μm filter-sterilized, and stored at 4° C.

Fluorescence Measurements

The emission spectra were recorded on a Varian Cary Eclipse fluorescence spectrophotometer (Varian Instruments, Walnut Creek, Calif.). All samples were measured in quartz cuvettes (Starna Cells, Inc., Atascadero, Calif.).

Response and Recovery Time Measurements

The response and recovery times of the binding proteins were studied in Slide-A-Lyzer® dialysis cassettes (PIERCE, Rockford, Ill.). Three cassettes were used for each measurement so that the error could be estimated. To measure the response time, 1 mL of protein solution (1.7 μM GBP, 1.3 μM GlnBP) was injected into each cassette, to which a buoy was then attached. A dean 500-mL beaker was filled with 400 mL of 10 mM phosphate butter with the desired glucose or glutamine concentration. The dialysis cassettes were then put into the beaker and gently stirred. The fluorescence intensity of the protein solutions was measured every 2-5 min until equilibrium was reached. To measure the recovery time, the cassettes were removed from the beaker and then placed into another beaker filled with 400 mL of fresh 10 mM phosphate buffer. Thereafter, the florescence intensity was measured every 20-60 min until new equilibrium was reached. Meanwhile, the buffer was replaced with fresh buffer every 30 min.

Fermentation and Cell Culture

The yeast seed culture consisted of 4 mg dry yeast cells (SAF Consumer Company, Atlanta, Ga.) in 20 mL of YEHD-rich medium (2% yeast extract, 1% soy peptone, and 2% glucose). The culture was incubated at 30° C. with shaking at 260 rpm for 8-10 h. The fermentation was carried out at 30° C. in a 500-mL shake flask containing 147 mL of YEHD medium and 3 mL of seed inoculum. Then 1.0 mL of broth sample was taken for analysis every 30-60 minutes. To avoid the change in glucose concentration after sampling, the samples were quickly cooled on ice to quench the cellular metabolism. After the optical density (OD) was measured with a Milton Roy Spectronic 401 spectrophotometer at 600 nm, the sample was centrifuged and the supernatant glucose concentrations were measured directly with a YSI 2700 Chemistry Analyzer and concurrently with the glucose biosensor described here by diluting 1 μL of sample 10,000 to 40,000 times.

The *E. coli* (JM105) seed culture consisted of 2% inoculum in 5 mL of LB medium incubated at 37° C. with shaking at 260 rpm for 8-10 h. The fermentations were carried out at 37° C. in a 500-mL shake flask, a 15-mL polypropylene tube, and on a 96-well plate. The volume of LB medium added to each fermentor was 150 mL, 5 mL, and 100 μL with 3% seed culture for the 150-mL fermentation and 5% for the other two. Samples were taken every 30-60 min. For the 150-mL fermentation, 1 mL of sample was taken each time and the glucose concentration and optical density were measured thereafter. For the 5-mL and 100-μL fermentations, only 1 μL of sample was taken each time and the optical density was measured only at the end of the fermentation. Glucose analysis was conducted in the same manner as in the yeast fermentation except that all samples were diluted 250 times.

The cells used in the cell culture came from two different cell lines, GM010178 and GM14649, both lymphoblasts from adult breast tissue. These cell lines were obtained commercially from Coriell Cell Repositories, and have been grown in a solution of 15% Fetal Bovine Serum in RPMI Medium 1640 with GlutaMAX™ (Gibco™, Grand Island, N.Y.). For the 100 mL cell culture, 50 mL of fresh medium was mixed with 50 mL of inoculum in a 250 mL polystyrene flask, and then incubated in a $CO_2$ incubator (Precision Scientific, Chicago, Ill.) until the color of the medium turned from red to yellow. 1 mL of sample was taken from the culture every 2 h for analysis. After sampling, the sample was quickly cooled on ice to quench the cellular metabolism. The glutamine concentration was then measured with a YSI 2700 Chemistry Analyzer and concurrently with the glutamine biosensor by diluting a small volume of sample 1,000 times. For the 100-μL cell culture, 50 μL of fresh medium was mixed with 50 μL of inoculum in a well on a 96-well plate, and then incubated in the $CO_2$ incubator. One microliter of sample was taken each time and the glutamine concentration was measured with the present biosensor thereafter.

Results and Discussion

Optical Spectrum

The mutant GBP and GlnBP each had a single cysteine residue at position 26 and position 179, respectively. The cysteine mutation allowed the proteins to be labeled with sulfhydryl-reactive dyes that exhibit polarity sensitive photo-physical properties with lower fluorescence intensity in more polar environment.

Figure 15:
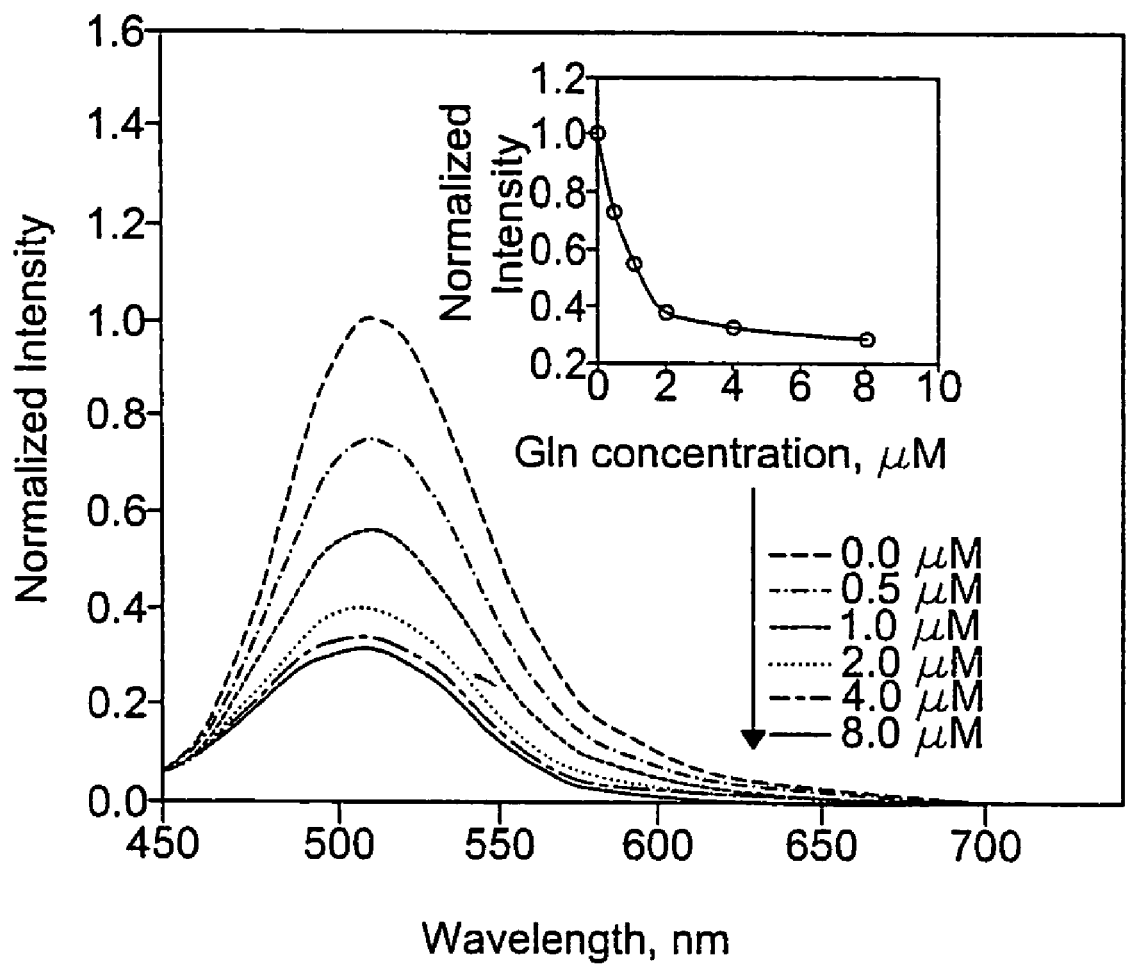
FIG. 15 shows the emission spectra of Acr-GlnBP with increasing concentrations of glutamine (GlnBP concentration=1.01 µM; excitation wavelength=360 nm). The inset of FIG. 15 shows changes in normalized emission intensity at 515 µm with glutamine concentrations.
Figure 16:
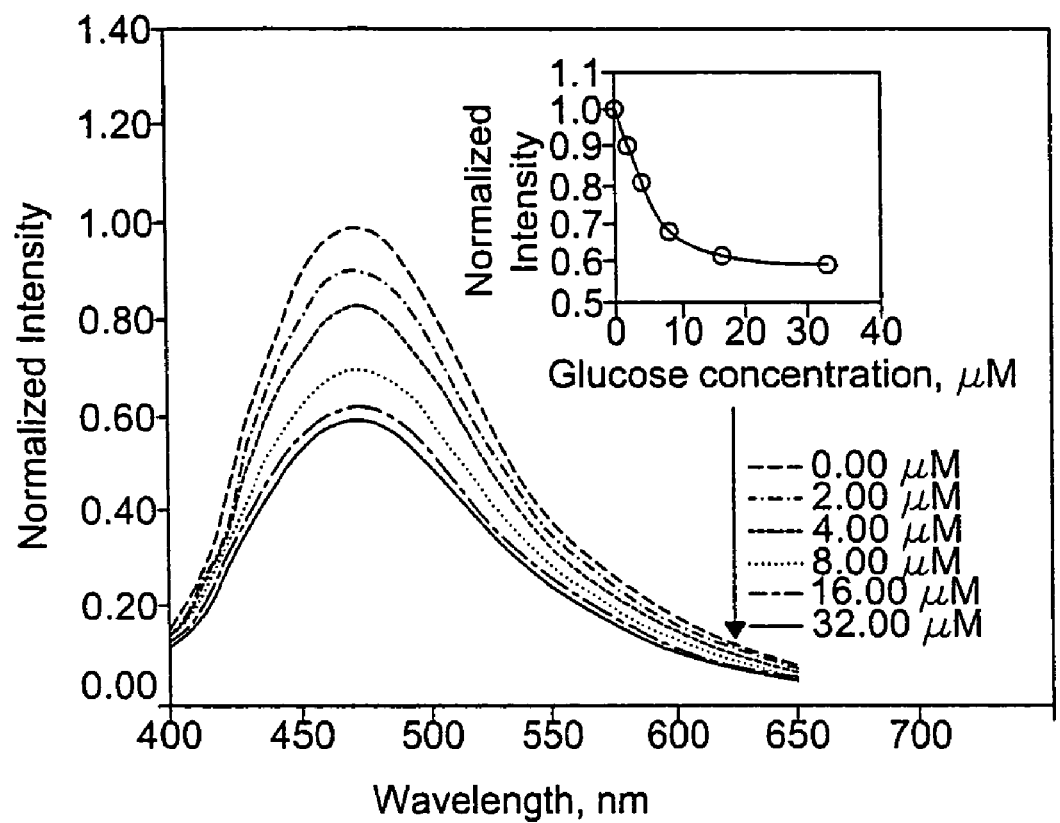
FIG. 16 shows the emission spectra of ANS-GBP with increasing glucose concentration (GBP concentration=8.1 µM; excitation wavelength=330 nm). The inset of FIG. 16 shows changes in normalized emission intensity with glucose concentrations.

The GlnBP labeled with acrylodan exhibited one emission maximum at 515 nm, which decreased in intensity with increasing concentration of glutamine (FIG. 15). While not wishing to be bound by theory, this decrease in intensity suggests that acrylodan was displaced into the more polar aqueous phase upon ligand binding. Like the acrylodan-labeled GlnBP, GBP labeled with ANS exhibited one emission maximum at 466 nm, which decreased in intensity with increasing concentration of glucose (FIG. 16). The calibration curves of these two biosensors are shown in the insets in FIGS. 15 and 16.

The apparent binding constants were calculated by fitting the experimental results to the binding isotherm (DATTEL-BAUM et al., Anal. Biochem., 291:89-95 (2001), which is incorporated by reference herein). The binding constants for the single-labeled and doubled-labeled GlnBP were calculated to be 0.23±0.01 μM and 0.28±0.03 μM, respectively. Both were in agreement with the reported value of 100-300 nM for the wild type (SOHANPAL et al., Sensors Actuators B, 11:547-552 (1993), which is incorporated by reference herein). While not wishing to be bound by theory, the reason for this agreement is believed to be that the position of the fluorophore is far from the binding site, consequently, the binding affinity is not greatly affected. The binding constant of GBP for glucose was calculated to be 0.78±0.07 μM, which also agrees well with the reported value of 0.8 μM (HELLINGA et al., Trends Biotechnol., 16:183-189 (1998), which is incorporated by reference herein).

Stability and Reproducibility

Figure 17:
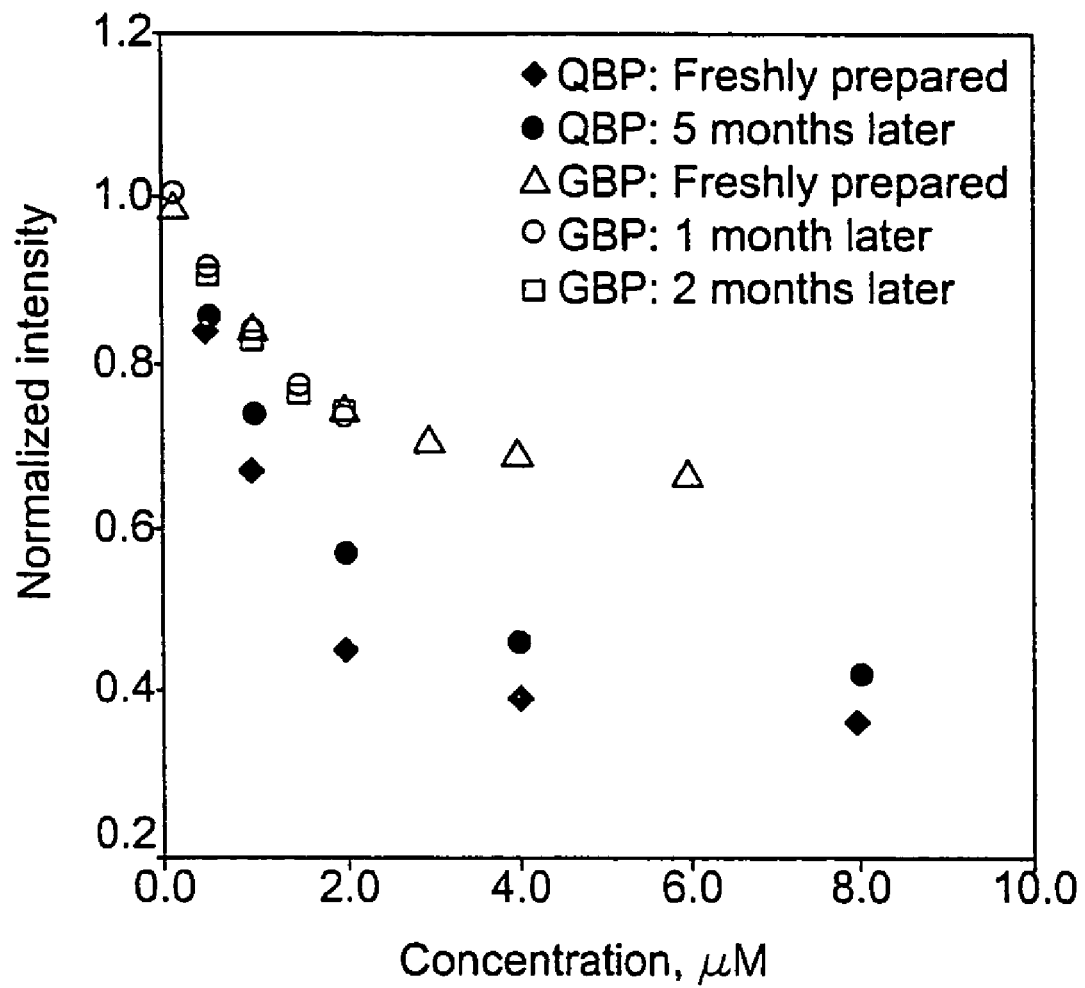
FIG. 17 shows the reproducibility of GlnBP (GlnBP=QBP) and GBP (GlnBP: concentration=1.01 µM, excitation wavelength=360 nm, emission wavelength=515 nm; GBP concentration=1.7 µM, excitation wavelength=330 nm, emission wavelength=466 am).

The stability of the binding proteins was determined by binding assays. The labeled binding proteins can be stored in phosphate buffer at 4° C. for at least 5 months. The reproducibility of the calibration curves is shown in FIG. 17, which shows that the sensitivity of GBP did not undergo any change during the testing period of 2 months. It also shows that the labeled GlnBP underwent some changes in 5 months after preparation, but was still responsive to glutamine. While not wishing to be bound by theory, factors that could have caused this change include fluorophore and protein. In any case, the recalibration of the biosensor during its use in fermentation or cell culture is unnecessary because fermentation or cell culture usually lasts from only several hours to a few days.

Responsive Ranges

The lower and upper detection limits are important properties of a sensor. The lower detection limit of the present sensing strategy was calculated from the experimental data according to its definition (Signal/Noise=3). The results in Table 5, below, show that the detection limit was mainly affected by the binding affinity of the protein, the concentration of the protein, and the quantum yield of the fluorophore. The binding affinity determines the magnitude of the responsive ranges. Therefore, the most effective way to change the responsive rages is to modify the structure of the binding site by mutagenesis. It should also be noted that the apparent binding constant may be affected by the fluorophore and the labeling position (BRENNAN et al., J. Phys. Chem., B, 104: 10100-10110 (2000); DATTELBAUM et al., Anal. Biochem., 291:89-95 (2001); and HELLINGA et al., Trends Biotechnol, 16:183-189 (1998), all of which are incorporated by reference herein), which, in turn, affects the responsive range.

TABLE 5

| Protein | Affinity Constant (μM) | Dye | Conc. (μM) | Lower Detection Limit (LDL) (μM) | Upper Detection Limit (UDL) (μM) | LDL/UDL |
|---|---|---|---|---|---|---|
| GBP | 0.78 | ANS | 1.7 | 0.3 | 10 | 33 |
| | | | 5.5 | 0.5 | 32 | 64 |
| GlnBP | 0.23 | Acrylodan | 0.87 | 0.03 | 3.2 | 107 |
| | | | 3.54 | 0.07 | 16 | 229 |

The effect of protein concentration on the responsive range is illustrated in Table 5, above. Although both detection Limits increased with the protein concentration, the lower detection limit increased only slightly while the upper detection limit increased almost proportionately. If the ratio of the upper detection Limit and lower detection limit is defined as the flexibility of the sensing range, the flexibility of the sensing range can increase greatly if the concentration of the binding protein is increased. The decrease of the lower detection limit with the decreasing the protein concentration allows us to adjust the sensing sensitivity. The lower the protein concentration, the higher the sensitivity but the responsive range will be narrower (GE et al., Biotech. Bioeng., 84(6): 723-731 (2003), which is incorporated by reference herein).

Comparing the detection limits of GBP and GlnBP shows that the lower detection Limit of GlnBP is about 10 times lower than that of GBP. This big difference was manly caused by the difference between the quantum yields of the two fluorophores. The acrylodan on the GlnBP has a much higher quantum yield than the ANS on the GBP. The reason is that a fluorophore with a higher quantum yield can give a much stronger signal for the same strength of excitation. As a result, the lower detection limit of the sensor can be greatly lowered and the flexibility of the sensing range can be significantly improved.

Response and Recovery Times

To verify the feasibility of the encapsulation method, the response and recovery times of the two binding proteins were studied in Slide-A-Lyzer® dialysis cassettes with a molecular weight cut off of 10,000 (PIERCE, Rockford, Ill.). Experimental results (FIG. 18) show that the response was fairly rapid for both binding proteins (around 5-12 min). However, compared with the extremely fast response in liquid (less that 1 s), the response time in dialysis cassettes suggested that this process was diffusion-limited. Compared with the relatively fast response, the recovery times for both binding proteins were relatively long. To facilitate the signal recovery, the effect of ultrasonic agitation on this process was tested. Unexpectedly, the signal recovery was actually delayed in ultrasound field. While not wishing to be bound by theory, the reason for this delay might be that agitation altered the positioning of the dye on the protein, making the dye more exposed to the environment.

To find a rationale for the slow signal recovery, computer simulations were conducted by using the reported kinetic parameters for the binding reaction between glutamine and GlnBP (WEINER et al., J. Biol. Chem., 246(22):6933-6941 (1971), which is incorporated by reference herein). The reported value of $k_a$ for the binding is $9.8 \times 10^7$ $M^{-1}s^{-1}$ and the $k_d$ for the dissociation is 16 $s^{-1}$. These two values yield a dissociation constant of 0.163 μM, which is close to that obtained in this study.

The mathematical model used for simulation was based on the following three assumptions:

1. The mass transfer resistance across the dialysis membrane is the only major resistance. All other mass transfer resistances are negligible.
2. No concentration differences exists throughout the space inside the dialysis membrane.
3. The concentration of the free substrate is always in equilibrium with the concentration of the bound substrate.

Based on the above assumptions, the following equation can be obtained by doing the mass balance of the substrate:

$$V \frac{d([A] + [EA])}{dt} = KS([A]_0 - [A]) \quad (18)$$

where V is the volume of the binding protein solution inside the dialysis membrane. [A] and [AE] are the concentrations of the substrate in free and bound state, respectively. t is time. K is the overall mass transfer coefficient. S is the area for mass transfer. $[A]_0$ is the concentration of the substrate outside the dialysis membrane. According to the third assumption:

$$A + E \Leftrightarrow EA \quad (19)$$

$$k_a[A][E] = k_d[EA] \quad (20)$$

$$[A] = \frac{k_d[EA]}{k_a([E]_T - [EA])} \quad (21)$$

where $k_a$ and $k_d$ are the rate constants for binding and dissociation, respectively. [E] is the concentration of the binding protein with no bound substrates. $[E]_T$ is the total concentration of the protein. Substitution of equation 21 into equation 18 gives:

$$\frac{d[EA]}{dt} = -\frac{KS}{V}\frac{k_d[EA]([E]_T - [EA])}{k_d[E]_T + k_a([E]_T - [EA])^2} \quad (22)$$

Equation (22) was used to simulate the response and recovery process.

Figure 19A:
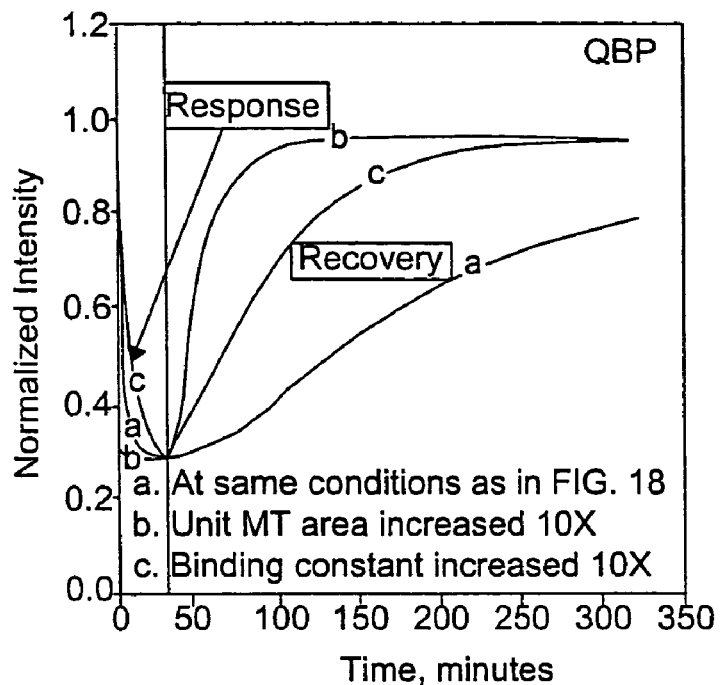
FIG. 19 shows simulated response and recovery curves for GlnBP (FIG. 19a) and GBP (FIG. 19b).
Figure 19B:
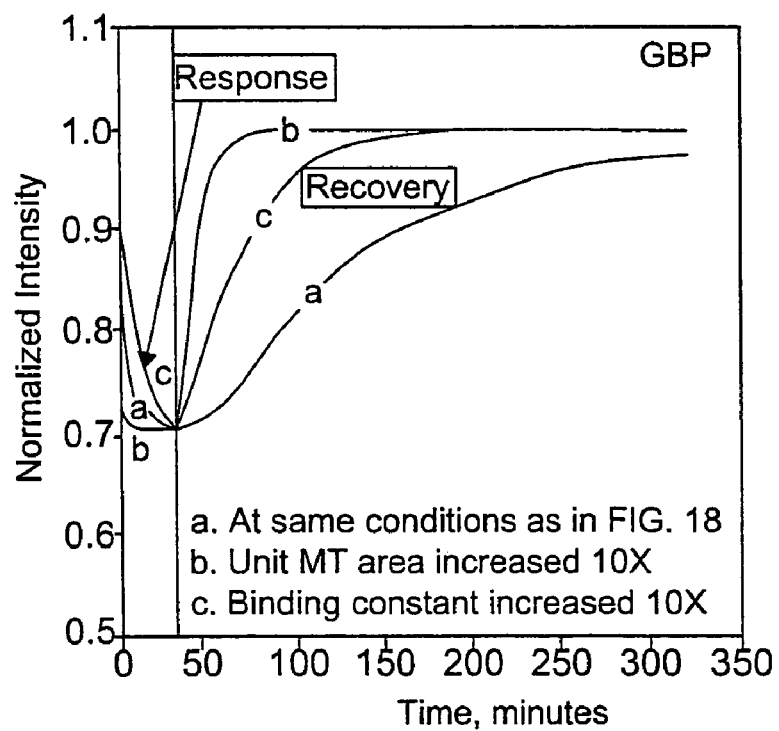

The calculated results show that when there is no mass-transfer resistance, the response and recovery both take less than 1 s (results not shown), showing that the binding of the ligand is completely reversible and the time needed to reach equilibrium is actually very fast in liquid. However, when the binding protein is encapsulated in a dialysis cassette, the response time is delayed by several minutes and the recovery time is delayed even longer to several hours (see FIG. 19). The simulated results for 90% response and 90% recovery times were calculated based on equation (22) and listed in Table 6, below. These results show that the binding constants and the mass transfer resistance are the two major factors that affect the response and recovery times. Because of the low dissociation constant, few free ligands exist in equilibrium with the bound ligands, resulting in a very small mass transfer driving force in the recovery process. Increasing the binding constants through mutagenesis and decreasing the mass transfer resistance are two solutions to this problem. Comparatively, the latter is much easier and more efficient in reducing the response and recovery times. Simulated results show that using dialysis tubing with a diameter of 1 mm or less and 10,000 MWCO, it is possible to reduce the recovery time to less than 30 min (Table 6, below).

TABLE 6

Figure 18:
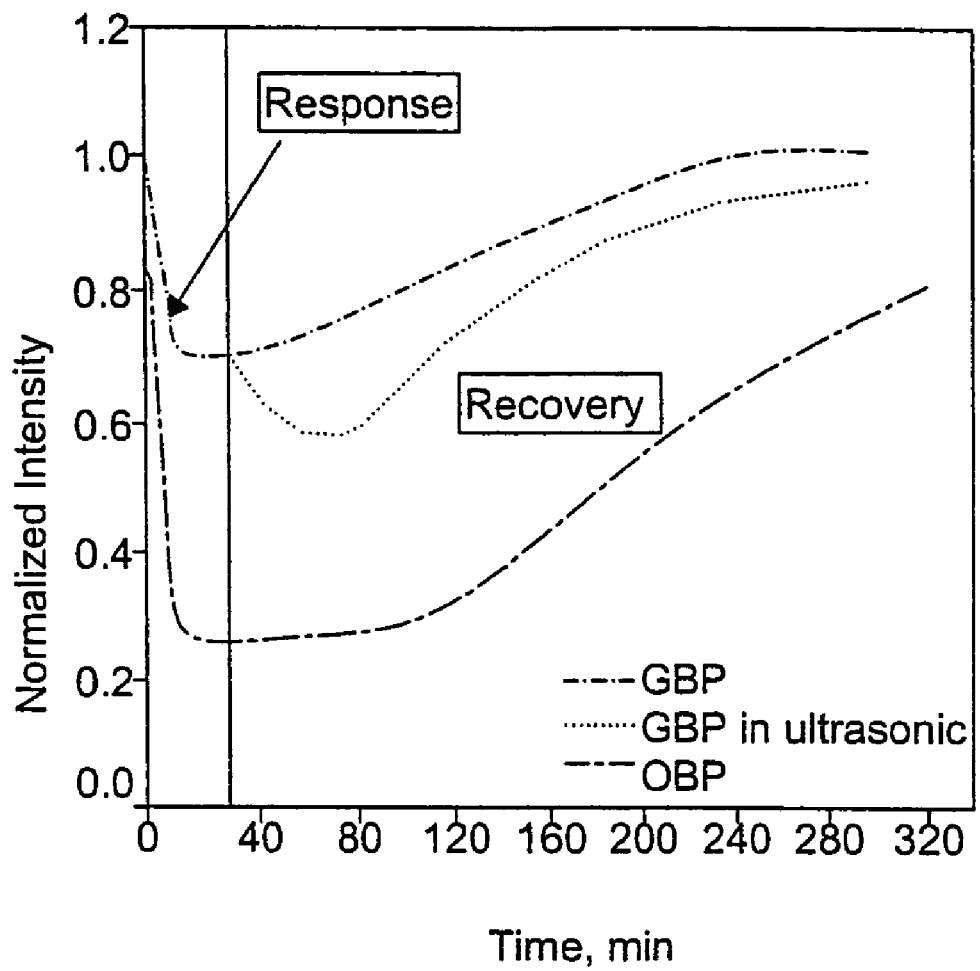
FIG. 18 shows the response and recovery times of GBP and GlnBP (GlnBP=QBP) in dialysis cassettes (GBP concentration=1.7 µM, excitation wavelength=330 mm, emission wavelength=466 rum; GlnBP concentration 1.3 µM, excitation wavelength=360 nm, emissions wavelength=515 nm).

|  | GlnBP | | GBP | |
| --- | --- | --- | --- | --- |
|  | Response (min) | Recovery (min) | Response (min) | Recovery (min) |
| At same conditions as FIG. 18 | 8 | 515 | 8 | 266 |
| $K_d$ increased 10× | 19 | 146 | 18 | 82 |
| Unit MT area increased 10× | 0.8 | 52 | 0.6 | 26 |

Applications in Fermentation and Cell Culture

Figure 20:
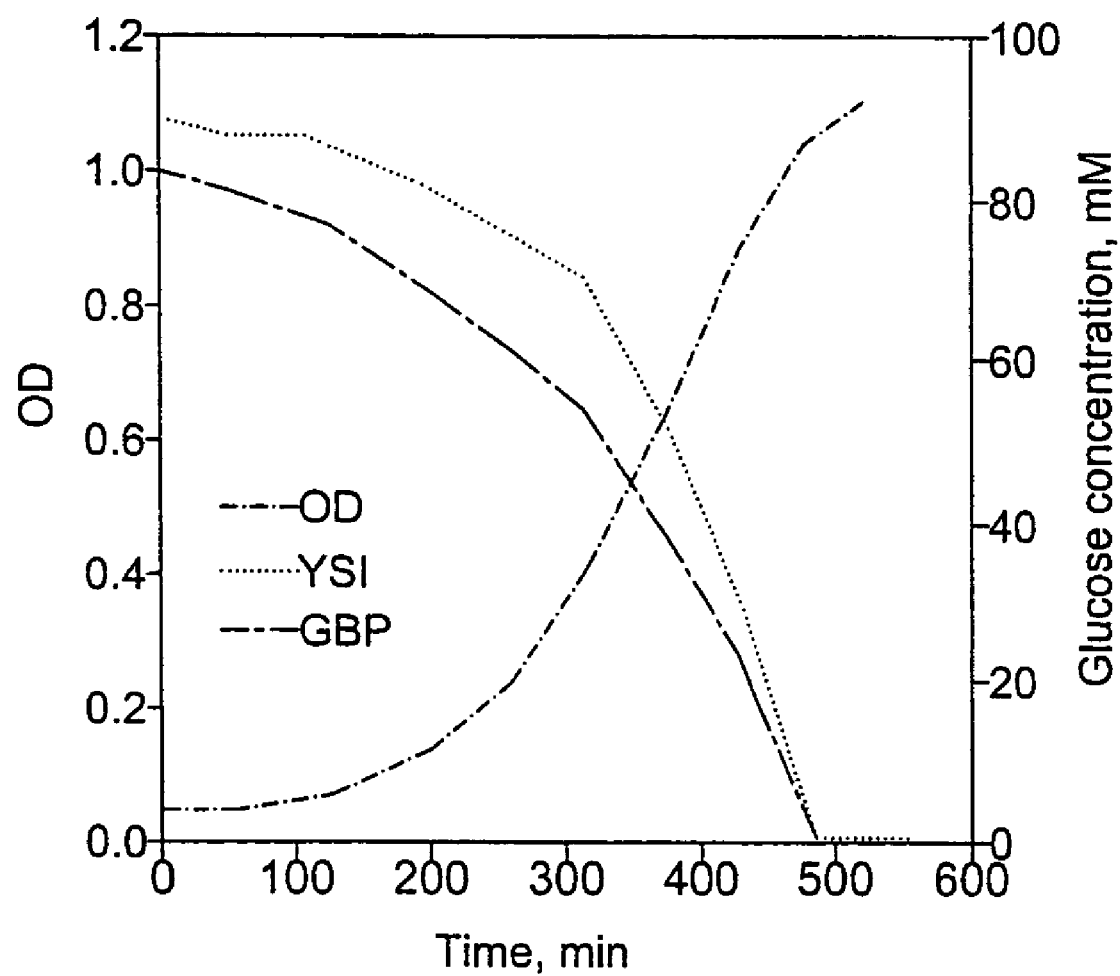
FIG. 20 shows a comparison of glucose concentrations, measured with a YSI 2700 Chemistry Analyzer® and GBP in yeast fermentation.

The applicability of the present sensing strategy was tested in a yeast fermentation, E. coli fermentation, and mammalian cell culture. The glucose concentrations were measured with both a YSI 2700 Chemistry Analyzer (Yellow Springs Instrument Co., Inc.) and the GBP. The YSI 2700 Chemistry Analyzer has a responsive range up to 140 mM and a lower detection limit (base on signal/noise=3) of 0.1 mM. GBP has a lower detection limit between 0.3-0.5 µM (Table 5). Because of this extremely high sensitivity, the responsive range of GBP can be expanded to several orders of magnitude by simply diluting the sample. For example, the samples analyzed using GBP were diluted 10,000 to 40,000 times while the samples analyzed with YSI were aspirated into the instrument as is (see FIG. 20). This dilution step does not only expand the responsive range. Just as importantly, it leads to the elimination or minimization of fluorescent interference in optically "dirty" media. For this reason, it is not difficult to obtain reliable data even from the UV-excitable ANS label of GBP. As shown in FIG. 20, although the glucose concentration readings were not completely identical for the two different methods, the trend was similar. While not wishing to be bound by theory, the presence of ascorbic acid in the baker's yeast, which tends to increase the YSI signal, might be one of the reasons for the disagreement. Ascorbic acid is added to the SAF yeast as a dough conditioner to help dough stretch easily (www.safyeast.com/catalog.html, which is incorporated by reference herein).

Figure 21A:
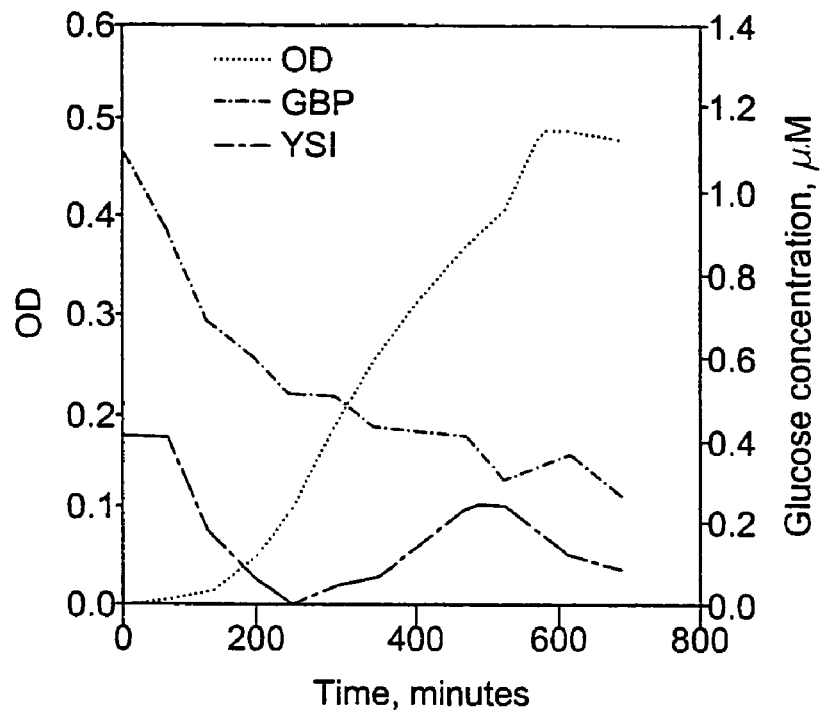
FIG. 21 shows changes in glucose concentration measured with GBP in *E. coli* fermentations (FIG. 21a) in a 500-mL shake flask, (FIG. 21b) in a 15-mL plastic tube and on a 96-well plate.

For the E. coli fermentation in 500-mL shake flask, the trend in glucose consumption as the cell density increases was clearly established from the data determined using the binding protein (FIG. 21a). In contrast, the YSI 2700 Chemistry Analyzer could not give reliable results because the glucose concentration in LB medium was close to the lower detection limit of YSI, which was measured to be 0.1 mM. Clearly, GBP is better at monitoring glucose concentrations at submillimolar levels.

Figure 21B:
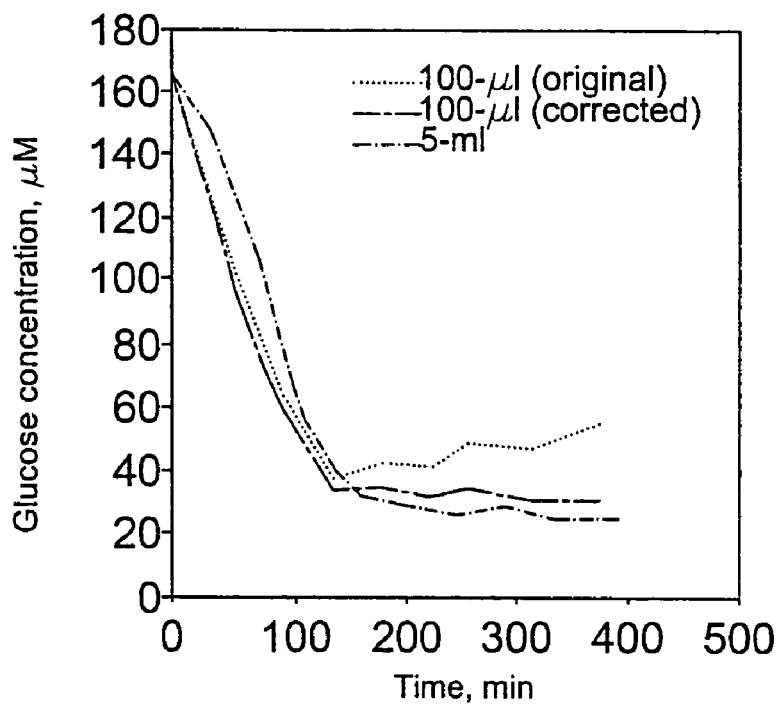

Another advantage afforded by the high sensitivity of GBP is that very small sample volumes (<1 µL) are required for analysis. This makes it applicable to microbioreactors (≈100 µL). This application is impossible for the YSI Chemistry Analyzer because its minimum sample volume is 5 µL, which is too high for microbioreactors. The changes in glucose concentration during the 5-mL fermentation and the 100-µL fermentation are shown in FIG. 21b. For the 100-µM fermentation, it was noted that the glucose concentration was somewhat affected by the evaporation of the medium, which tends to increase the concentrations of the solutions. However, after correcting the effect of volume change caused by evaporation, it was found that the glucose concentration profiles for the two different scales of fermentations are actually quite similar.

Figure 22A:
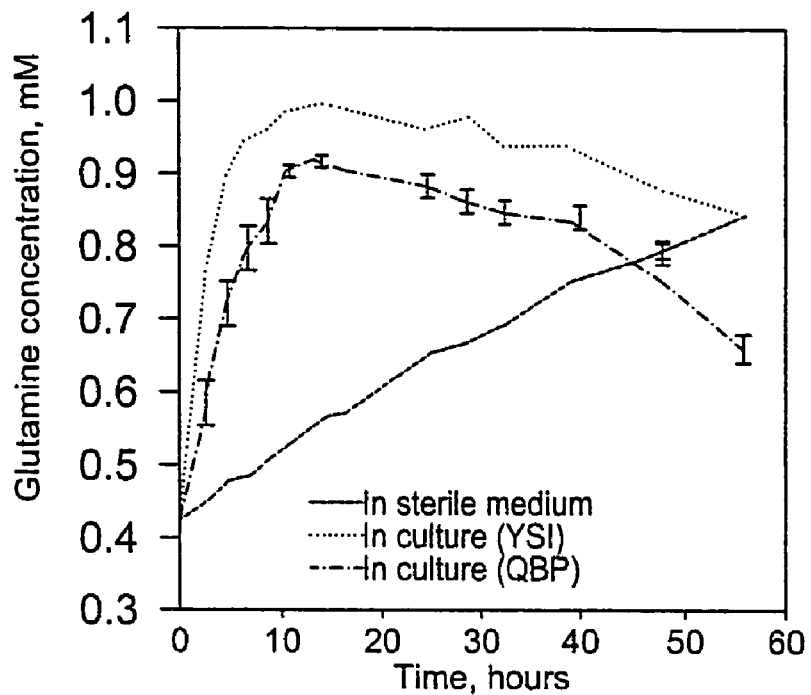
FIG. 22 shows changes in glutamine concentration measured with a YSI 2700 Chemistry Analyzer and GlnBP in cell culture (FIG. 22a) in a 250-mL polystyrene flask for cell culture (cell line GM14649), and (FIG. 22b) on a 96-well plate (cell GM010178).

The GlnBP sensor was tested in a lymphoblast culture. The glutamine concentration profiles during the 100-mL cell culture are shown in FIG. 22a. The gradual increase in glutamine concentration in the sterile medium in the absence of cells was caused by the gradual release of glutamine from GlutaMAX™, a dipeptide conjugate (L-alanyl-L-glutamine) used as the L-glutamine source in a stabilized form (URL: http://www.invitrogen.com, which is incorporated by reference herein). The dissociation of the GlutaMAX™ dipeptide is accelerated by aminopeptidases within the cell. At the early stage of the cell culture, the concentration of the dipeptide was high. The dissociation rate of the dipeptide was greater than the utilization rate of the glutamine released. As a result, some of the glutamine molecules diffused out of the cells and accumulate in the medium (BRAND et al., Metabolism, 38(8), suppl 1:29-33 (1989), which is incorporated by reference herein). While not wishing to be bound by theory, it is believed that this is the reason why the glutamine concentration increased more rapidly when cells were present.

As in the determination of glucose, analysis of glutamine by the GlnBP sensor was compared to the YSI Chemistry Analyzer. Determination of glutamine using YSI is a complicated process. The YSI glutamine biosensor is a glutaminase and glutamate oxidase dual enzyme sensor (URL: http://www.ysi.com, which is incorporated by reference herein). The glutaminase converts glutamine to glutamate and ammonia. The glutamate thus produced is then oxidized by glutamate oxidase to α-ketoglutarate, ammonia, and hydrogen peroxide. The hydrogen peroxide that is released is detected at the platinum electrode. Since glutamate oxidase can also detect the glutamate that is already present in the media, the reading of the glutamine sensor is actually the sum of glutamine and glutamate in the media. To determine the concentration of glutamine alone, a second sensor containing only the glutamate oxidase has to be used initially to determine the glutamate concentrations. This value is then subtracted from the sum to get the glutamine concentration. For the present experiment, only the glutamine sensor was used, and therefore includes both glutamine and glutamate. GlnBP on the other hand, is responsive to glutamine but not to glutamate. This explains the higher readings of YSI compared to those of GlnBP as seen in FIG. 22a. The highly sensitive, more straightforward, and highly selective measurement of glutamine by GlnBP is believed to be an improvement from the current industry standard for glutamine analysis.

Figure 22B:
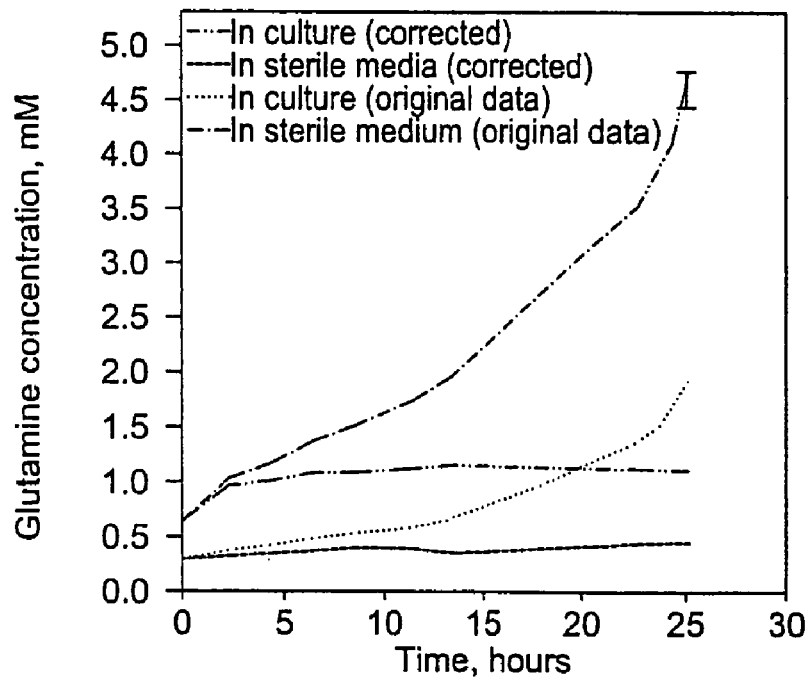

The 0.03-0.07 μM lower detection limit (Table 5) for the acrylodan-labeled GlnBP allows for sample volumes smaller than those for GBP. The sample volume for the assay described here can be as small as 500 nl or even less. This makes it applicable to microscale cell cultures as shown in FIG. 22b for the glutamine concentration profile in a 100-μL cell culture. In this case, the relatively large sample volume requirement of YSI (at least 5 μL) prevented its application. As in the small-scale E. coli fermentation described previously, the glutamine concentration was also affected by evaporation of the medium in small-scale cell cultures. Thus, the effect of volume change must be taken into account. The effect in this case was much greater as the duration of the experiment was much longer. To correct the effect of volume change, the volume of the medium was measured at the beginning and the end of the cell culture. The volume of the medium during the cell culture was then estimated by assuming a linear decease in volume. This assumption of linear decrease in volume is reasonable because the surface area for evaporation is constant.

The foregoing embodiments and advantages are merely exemplary and are not to be construed as limiting the present invention. The description of the present invention is intended to be illustrative, and not to limit the scope of the claims. Many alternatives, modifications, and variations will be apparent to those skilled in the art.

Having now fully described this invention, it will be understood to those of ordinary skill in the art that the methods of the present invention can be carried out with a wide and equivalent range of conditions, compositions, and other parameters without departing from the scope of the invention or any embodiments thereof.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

---

---

What is claimed is:

1. A protein sensing molecule that is capable of binding an analyte in a sample, the protein sensing molecule comprising:
   a first detectable quality that changes in a concentration dependent manner when the protein sensing molecule is bound to the analyte; and
   a second detectable quality, comprising a long-lived metal complex label, that undergoes a sufficiently small percentage change when the protein sensing molecule is bound to the analyte to function as a reference.

2. The protein of claim 1, wherein the first detectable quality comprises a label.

3. The protein of claim 1, wherein the first detectable quality comprises a label that is different from the label of the second detectable quality.

4. The protein of claim 1, wherein the first detectable quality comprises a polarity-sensitive fluorophore label.

5. The protein of claim 1, wherein the first detectable quality comprises at least one of acrylodan and anilino-naphthalene sulfonate.

6. The protein of claim 1, wherein the second detectable quality undergoes a change of less than 5% when the protein sensing molecule is bound to the analyte.

7. The protein of claim 1, wherein the analyte comprises a naturally occurring sugar, sugar derivative, or sugar analog.

8. The protein of claim 1, wherein the analyte comprises at least one of glucose, lactose, galactose, sucrose, and maltose.

9. The protein of claim 1, wherein analyte binding causes the first detectable quality to be shielded.

10. The protein of claim 1, wherein analyte binding causes the first detectable quality to be unshielded.

11. The protein of claim 1, wherein the protein comprises an analyte binding site.

12. The protein of claim 1, wherein the protein comprises at least one of modified glutamine-binding protein, modified glucose-binding protein, modified hexokinase, and modified glucokinase.

13. The protein of claim 12, wherein the protein is modified by substituting at least one cysteine residue therein.

14. The protein of claim 12, wherein the protein is modified by substituting two cysteine residues therein.

15. A protein sensing molecule that is capable of binding an analyte in a sample, the protein sensing molecule comprising:

- a first detectable quality that changes in a concentration dependent manner when the protein sensing molecule is bound to the analyte; and
- a second detectable quality, comprising a ruthenium complex label or osmium complex label, that undergoes a sufficiently small percentage change when the protein sensing molecule is bound to the analyte to function as a reference.

16. A protein sensing molecule that is capable of binding an analyte, comprising glutamine, in a sample, the protein sensing molecule comprising:

- a first detectable quality that changes in a concentration dependent manner when the protein sensing molecule is bound to the analyte; and
- a second detectable quality that undergoes a sufficiently small percentage change when the protein sensing molecule is bound to the analyte to function as a reference.

* * * * *